(12) United States Patent
Deckner et al.

(10) Patent No.: US 10,596,079 B2
(45) Date of Patent: Mar. 24, 2020

(54) HIGH EFFICIENCY SUNSCREEN COMPOSITION

(71) Applicant: DECKNER CONSULTING SERVICES, LLC, Cincinnati, OH (US)

(72) Inventors: George Endel Deckner, Cincinnati, OH (US); Nickolas Huss, Maywood, NJ (US)

(73) Assignee: Deckner Consulting Services, LLC, Cincinnati, OH (US)

( * ) Notice: Subject to any disclaimer, the term of this patent is extended or adjusted under 35 U.S.C. 154(b) by 0 days.

(21) Appl. No.: 15/762,685

(22) PCT Filed: Sep. 26, 2016

(86) PCT No.: PCT/US2016/053762
§ 371 (c)(1),
(2) Date: Mar. 23, 2018

(87) PCT Pub. No.: WO2017/053959
PCT Pub. Date: Mar. 30, 2017

(65) Prior Publication Data
US 2018/0263866 A1 Sep. 20, 2018

Related U.S. Application Data

(60) Provisional application No. 62/222,923, filed on Sep. 24, 2015.

(51) Int. Cl.
*A61K 8/06* (2006.01)
*A61Q 17/04* (2006.01)
(Continued)

(52) U.S. Cl.
CPC ............ *A61K 8/062* (2013.01); *A61K 8/0241* (2013.01); *A61K 8/042* (2013.01); *A61K 8/11* (2013.01);
(Continued)

(58) Field of Classification Search
None
See application file for complete search history.

(56) References Cited

U.S. PATENT DOCUMENTS 5,500,223 A 3/1996 Behan et al.
5,733,531 A 3/1998 Mitchnick et al.
(Continued)

FOREIGN PATENT DOCUMENTS

EP 1627668 A1 2/2006
WO WO-2007/075747 A2 7/2007
(Continued)

OTHER PUBLICATIONS

International Application No. PCT/US2016/053762, International Preliminary Report on Patentability, dated Mar. 27, 2018.
(Continued)

*Primary Examiner* — Robert A Wax
*Assistant Examiner* — Melissa S Mercier
(74) *Attorney, Agent, or Firm* — Carter Ledyard & Milburn LLP

(57) ABSTRACT

Disclosed herein are oil-in-water dispersions and sunscreen compositions that contain them, which exhibit high in vivo sun protection factor (SPF) efficiency due to the ability of the dispersions to both absorb and scatter ultraviolet (UV) light. These high efficiency sunscreen compositions include discrete oil particles that are enclosed within a solid coating and dispersed in an aqueous phase, wherein each oil particle contains an organic ultraviolet A (UVA) and/or an organic ultraviolet B (UVB) absorbing compound, and optionally a photo stabilizer.

26 Claims, 1 Drawing Sheet

(51) Int. Cl.

| | |
|---|---|
| *A61K 8/25* | (2006.01) |
| *A61K 8/11* | (2006.01) |
| *A61P 17/16* | (2006.01) |
| *A61K 8/02* | (2006.01) |
| *A61K 8/04* | (2006.01) |
| *A61K 8/35* | (2006.01) |
| *A61K 8/37* | (2006.01) |
| *A61K 8/40* | (2006.01) |
| *A61K 8/41* | (2006.01) |
| *A61K 8/49* | (2006.01) |
| *A61K 8/81* | (2006.01) |

(52) U.S. Cl.
CPC ............... *A61K 8/25* (2013.01); *A61K 8/35* (2013.01); *A61K 8/37* (2013.01); *A61K 8/40* (2013.01); *A61K 8/415* (2013.01); *A61K 8/4966* (2013.01); *A61K 8/8152* (2013.01); *A61K 8/8182* (2013.01); *A61P 17/16* (2018.01); *A61Q 17/04* (2013.01); *A61K 2800/21* (2013.01); *A61K 2800/30* (2013.01); *A61K 2800/412* (2013.01)

(56) References Cited

U.S. PATENT DOCUMENTS

| | | |
|---|---|---|
| 5,783,174 A | 7/1998 | Deckner |
| 6,083,048 A | 7/2000 | Yamaguchi |
| 6,379,680 B2 | 4/2002 | Gers-Barlag et al. |
| 6,391,321 B1 | 5/2002 | Gers-Barlag et al. |
| 6,410,035 B1 | 6/2002 | Gers-Barlag et al. |
| 6,428,796 B1 | 8/2002 | Gers-Barlag et al. |
| 6,436,375 B1* | 8/2002 | Lapidot .................. A61K 8/042 424/400 |
| 6,436,376 B1 | 8/2002 | Hansenne et al. |
| 6,440,399 B1 | 8/2002 | Gers-Barlag et al. |
| 6,558,683 B2 | 5/2003 | Gers-Barlag et al. |
| 6,579,529 B2 | 6/2003 | Gers-Barlag et al. |
| 6,582,707 B2 | 6/2003 | Gers-Barlag et al. |
| 6,592,883 B1 | 7/2003 | Gers-Barlag et al. |
| 6,692,755 B2 | 2/2004 | Gers-Barlag et al. |
| 6,767,547 B2 | 7/2004 | Gers-Barlag et al. |
| 6,838,088 B2 | 1/2005 | Gers-Barlag et al. |
| 6,881,415 B1 | 4/2005 | Gers-Barlag et al. |
| 7,037,511 B1 | 5/2006 | Gers-Barlag et al. |
| 7,186,415 B1 | 3/2007 | Gers-Barlag et al. |
| 7,892,524 B2 | 2/2011 | Polonka et al. |
| 7,914,772 B2 | 3/2011 | Polonka et al. |
| 8,110,284 B2* | 2/2012 | Naigertsik ............. A01N 25/28 428/321.1 |
| 8,524,203 B2 | 9/2013 | Polonka |
| 8,652,449 B1 | 2/2014 | Halpern et al. |
| 8,685,425 B2 | 4/2014 | Speaker |
| 2003/0235540 A1 | 12/2003 | Herzog |
| 2005/0266055 A1 | 12/2005 | Stiller et al. |
| 2006/0263402 A1 | 11/2006 | Deckner et al. |
| 2006/0292095 A1 | 12/2006 | Biatry et al. |
| 2007/0086962 A1* | 4/2007 | Bandyopadhyay ...... A61K 8/35 424/59 |
| 2011/0236447 A1 | 9/2011 | Yoshimura et al. |
| 2014/0134255 A1 | 5/2014 | Saito et al. |
| 2014/0341954 A1 | 11/2014 | Bergeron et al. |
| 2014/0341981 A1 | 11/2014 | Bergeron et al. |
| 2015/0118273 A1 | 4/2015 | Polonka et al. |
| 2015/0233871 A1 | 8/2015 | Zeng et al. |

FOREIGN PATENT DOCUMENTS

| | | |
|---|---|---|
| WO | WO-2014/132261 A2 | 9/2014 |
| WO | WO-2014/135360 A1 | 9/2014 |
| WO | WO-2015/126874 A1 | 8/2015 |

OTHER PUBLICATIONS

International Application No. PCT/US2016/053762, International Search Report and Written Opinion, dated Dec. 27, 2016.

Popa et al., Co-encapsulation of a mixture of antioxidant and sunscreen agents into solid lipid nanoparticles, U.P.B. Sci. Bull., Series B, 76(2):45-56 (2014).

European Patent Application No. 16849861.6, Extended European Search Report, dated Apr. 1, 2019.

\* cited by examiner

HIGH EFFICIENCY SUNSCREEN COMPOSITION

CROSS-REFERENCE TO RELATED APPLICATION

This application is filed pursuant to 35 U.S.C. § 371 as a U.S. National Phase Application of International Application No. PCT/US2016/053762 (filed on Sep. 26, 2016), claiming the benefit under 35 U.S.C. § 119(e) of U.S. Provisional Patent Application Ser. No. 62/222,923 filed Sep. 24, 2015, the disclosures of which are each hereby incorporated by reference.

BACKGROUND

Field of the Disclosure

The present disclosure is directed to compositions comprising oil-in-water dispersions that include an oil phase composed of discrete oil particles coated with a solid material and dispersed in an aqueous phase; and each oil particle contains one or both of an organic ultraviolet A (UVA) absorbing compound or an organic ultraviolet B (UVB) absorbing compound.

Description of Related Technology

Sunscreen is a vital tool that can help prevent UV radiation-induced cancer and skin photoaging. Commercially available sunscreen compositions, however, often exhibit less than optimal in vivo SPF efficiency and photo stability. For example, the average in vivo efficiency of sunscreen compositions is about 1.6 SPF units per 1 wt. % sunscreen composition, based on the total weight of the composition (for SPF 15 and 30), with best-in-class metal oxide-based and organic-based sunscreen formulations exhibiting in vivo efficiencies of only about 6 and 4 SPF units, respectively, per 1 wt. % sunscreen composition. Further, broad-spectrum sunscreen compositions are highly recommended because they protect against both UVA and UVB irradiation. However, these compositions are inherently photounstable due to the interaction of the UVA and UVB absorbers with each other, and often require the inclusion of a photostabilizer. Because of the inefficiency and photoinstability of traditional sunscreen formulations, even when they include a photostabilizer, UV absorbers must often be present in the formulations in relatively high concentrations to produce an adequate effect. For example, sunscreens having SPF values of 15 or 30 often require about 10 wt. % to 20 wt. % of UV active compounds, respectively, based on the total weight of the sunscreen composition. Including such a high concentration of UV absorbers in a sunscreen formulation, however, can be problematic because of the tendency of the absorbers to penetrate into a user's skin where they can interact with living tissues and/or migrate across skin, reducing SPF over time, and cause eye stinging.

Sunscreen manufacturers have attempted to improve the in vivo SPF efficiency and photostability of broad range sunscreen compositions by separating the UVA and UVB absorbers from each other, thereby preventing interactions that destabilize the UVA absorbers.

Some manufacturers have encapsulated organic UVA and UVB absorbers into solid lipid nanoparticles ("SLNs"). SLNs are generally spherical particles with average diameters between 50 and 500 µm that include a lipophilic core stabilized by surfactants, such as polyamide-3 (e.g., OLEOCRAFT technology by Croda, present in SYLVACLEAR and UNICLEAR sunscreens). See, e.g., U.S. Pat. Nos. 7,914,772; 7,892,524; and 8,524,203 and U.S. Patent Application Publication Nos. 2015/118273 and 2007/0086962 (to Unilever); U.S. Pat. Nos. 6,436,376 and 8,652,449 and U.S. Patent Application Publication No. 2006/0292095 (to L'Oreal); and U.S. Patent Application Publication No. 2003/0235540 (to Bernd Herzog), each incorporated by reference in its entirety. See also, Popa, et al., *Co-Encapsulation of a mixture of Antioxidant and Sunscreen Agents Into Solid Lipid Nanoparticles*, U.P.B. Sci. Bull., Series B, 76(2):45-56 (2014), which describes the co-encapsulation of an organic sunscreen material (octocrylene) and an antioxidant (Luteolin) together into SLNs. Although sunscreen compositions containing UV absorbers encapsulated in SLNs exhibit improved photostability, they display poor in vivo SPF efficiency (e.g., 2.3 SPF units per 1 wt. % sunscreen composition). Further, SLNs often require the use of high wax levels, which has a negative effect on skin feel and consumer acceptance. Further still, in many commercial formulations, the UVA and UVB absorbers are often present in the same oil phase, allowing them to interact with, and destabilize, each other.

Other manufacturers have encapsulated UV absorbers using plant-based materials. For example, Botaneco has separately encapsulated organic UVA and UVB absorbers in oleosomes using its HYDRESIA technology. The oleosomes include a center core of plant oils and vitamin E surrounded by a phospholipid membrane, and are stabilized by the protein oleosin. Over time, however, these oleosomes release the UV absorbers inside by collapsing on the skin, allowing the UVA and UVB absorbers to interact with and destabilize each other, and also allowing the absorbers to penetrate the skin.

Sol-Gel Technologies describes separately encapsulated UVA and UVB absorbers in silica glass (see e.g., U.S. Pat. No. 6,436,375, incorporated herein by reference in its entirety), licensed to Merck as the EUSOLEX UV-PEARLS technology. The silica glass encapsulation prevents the UVA and UVB absorbers from interacting with each other, which photostabilizes them. However, sunscreen compositions containing these microparticles exhibit only mediocre in vivo SPF efficiency, such as 0.9 to 1.8 SPF units per 1 wt. % sunscreen composition.

Other manufacturers have attempted to separately encapsulate UVA and UVB absorbers using various different technologies. Although the sunscreen compositions containing these separately encapsulated UVA and UVB absorbers can exhibit improved photostability, they all display poor or mediocre in vivo SPF efficiency. For example, Capsulent Technology has encapsulated oxybenzone by precipitating a cationic surfactant with a soluble anionic polymer to form Lewis acid-Lewis base salt walls. See U.S. Pat. No. 8,685,425 to Tycho Speaker, which is incorporated herein by reference in its entirety. However, these capsules easily break when applied to the skin. Id. at paragraph [0035]. Tagra Biotechnology has encapsulated organic and inorganic UV filters in unbreakable, transparent microcapsules using its SUNCAPS technology (see PCT Publication No. 2014/132261). However, sunscreen compositions containing UV absorbers enclosed in SUNCAPS displays an in vivo SPF efficiency of only about 2.7 SPF units per 1% sunscreen composition. Sunsmart has provided sunscreen-encapsulated particles formed from a matrix composed of a wax or polymer (e.g., oils, lipids, protein derivatives, alkylated vinylpyrrolidone polymers, long chain alcohols, long chain fatty acids, ethylene-acrylic acid copolymers, and ethylene-vinyl acetate copolymers). See, e.g., U.S. Pat. No. 5,733,531, which is incorporated herein by reference in its entirety. However, sunscreen formulations containing these particles also exhibit poor SPF efficiency. For example, the in vivo SPF efficiency for 5% octinoxate is 3.3 SPF units per 1% sunscreen composition. These capsules also require a high wax level, resulting in poor consumer acceptance. Other sunscreen formulations containing encapsulated UVA and UVB absorbers are described in International Patent Application Publication Nos. 2007/075747 (to Schering Plough Healthcare) and 2014/135360 (to Unilever), each incorporated herein by reference in its entirety.

Sunscreen manufacturers also have attempted to improve the photostability of broad range sunscreen compositions by encapsulating UVA and UVB absorbers in Pickering emulsions, which are emulsions that are stabilized by solid particles. See, e.g., U.S. Patent Application Nos. 2014/0134255 (to Shiseido) and 2014/0341981 and 2014/0341954 (to L'Oreal) and U.S. Pat. No. 5,500,223 (to Unilever), each incorporated herein by reference in its entirety. The known sunscreen compositions containing Pickering emulsions, however, also display poor in vivo SPF efficiency. Beiersdorf also describes sunscreen compositions containing UV active materials in Pickering emulsions. See, e.g., U.S. Pat. Nos. 6,379,680; 6,391,321; 6,410,035; 6,428,796; 6,440,399; 6,558,683; 6,579,529; 6,582,707; 6,592,883; 6,692,755; 6,767,547; 6,083,048; 6,838,088; 6,881,415; 7,037,511; and 7,186,415; U.S. Patent Application Publication No. 2005/0266055; and EP Patent No. 1627668, each incorporated herein by reference in its entirety. The Beiersdorf materials, however, also display poor in vivo SPF efficiency. Further, many of the sunscreen formulations that contain Pickering emulsion include the UVA and UVB absorbers in the same oil phase, allowing them to interact with, and destabilize, each other.

Although sunscreen manufacturers have made great strides in developing sunscreen compositions having improved photo stability, the improved photostability has not resulted in compositions that also have high in vivo SPF efficiency. Therefore, there is a need for sunscreen compositions that exhibit excellent photostability and high in vivo SPF efficiency, which would allow a lower concentration of UV absorbers to be present in the compositions, and also that limit or prevent the penetration of UV absorbers into a user's skin.

SUMMARY

In one aspect, disclosed herein is a sunscreen composition comprising an oil-in-water dispersion that includes an oil phase composed of discrete oil particles, each oil particle coated with a solid material, and each oil particle comprising: (i) an organic UVA absorber present in an amount in a range from about 10 wt. % to about 70 wt. %, based on the total weight of the oil particle, (ii) an organic UVB absorber present in an amount in a range from about 30 wt. % to about 90 wt. %, based on the total weight of the oil particle, and (iii) a photostabilizer present in an amount in a range of about 10 wt. % to about 20 wt. %, based on the total weight of the oil particle. The oil-in-water dispersion is free of a metal oxide, and the oil particles are present in an amount in a range from about 50 wt. % to about 80 wt. %, based on the total weight of the dispersion.

In another aspect, disclosed herein is a sunscreen composition comprising an oil-in-water dispersion that includes an oil phase composed of discrete oil particles, each oil particle coated with a solid material, and each oil particle comprising: (i) an organic UVA absorber present in an amount in a range from about 10 wt. % to about 70 wt. %, based on the total weight of the oil particle; and (ii) an organic UVB absorber selected from the group consisting of octocrylene, oxybenzone, methylbenzylidene camphor, and combinations thereof, and present in an amount in a range from about 30 wt. % to about 90 wt. %, based on the total weight of the oil particle. The oil-in-water dispersion is free of a metal oxide, and the oil particles are present in an amount in a range from about 50 wt. % to about 80 wt. %, based on the total weight of the dispersion.

The UVA absorber can be present in an amount in a range of about 20 wt. % to about 70 wt. %, based on the total weight of the oil particle. The UVB absorber can be present in an amount in a range of about 40 wt. % to about 90 wt. %, or about 60 wt. % to about 90 wt. %, based on the total weight of the oil particle.

The photostabilizer, when present, can be selected from the group consisting of octocrylene, diethylhexyl naphthalate, undecylcrylene dimethicone, ethyl hexyl methoxycrylene, polyester-8, polyester 25, trimethoxybenzylidene pentanedione, diethylhexyl syringlidene malonate, tetramethyl hydroxy piperidinol, benzotriazole dodecyl p-cresol, sodium benzotriazole butyl phenol sulfonate, and combinations thereof. In some cases, the photostabilizer is octocrylene, diethylhexyl naphthalate, ethyl hexyl methoxycrylene, or combinations thereof. For example, the photostabilizer can be octocrylene.

In yet another aspect, disclosed herein is a sunscreen composition comprising an oil-in-water dispersion that includes an oil phase composed of first and second discrete oil particles, each oil particle coated with a solid material. The first oil particles include an organic UVA absorber present in an amount in a range from about 10 wt. % to about 100 wt. %, based on the total weight of the first oil particles, and are free of a UVB absorber. The second oil particles include an organic UVB absorber present in an amount in a range from about 30 wt. % to about 100 wt. %, based on the total weight of the second oil particles, and are free of a UVA absorber. The oil-in-water dispersion is free of a metal oxide, and the oil particles are present in an amount in a range from about 50 wt. % to about 80 wt. %, based on the total weight of the dispersion.

The UVA absorber can be present in an amount in a range of about 20 wt. % to about 100 wt. %, based on the total weight of the oil particle. The UVB absorber can be present in an amount in a range of about 40 wt. % to about 100 wt. %, or about 60 wt. % to about 100 wt. %, based on the total weight of the oil particle.

In some embodiments, the oil particles can present in an amount in a range from about 50 wt. % to about 70 wt. %, or about 50 wt. % to about 60 wt. %, based on the total weight of the dispersion.

In various embodiments, the oil particles can have a particle size in a range from about 0.5 µm to about 200 µm, or about 0.5 µm to about 100 µm, or about 0.5 µm to about 10 µm.

In some cases, the UVA absorber is selected from the group consisting of bemotrizinol, avobenzone, bisdisulizole disodium, meradimate, bisoctotrizole, ecamisule, diethylamino hydroxybenzoyl methyl benzoate, drometrizole trisiloxane and combinations thereof. In various cases, the UVA absorber is selected from the group consisting of avobenzone, oxybenzone, bemotrizinol, diethylamino hydroxybenzoyl methyl benzoate, and combinations thereof. For example, the UVA absorber can be avobenzone.

In some embodiments, the UVB absorber is selected from the group consisting of enzacamene, oxybenzone, octinoxate, octisalate, octyltriazone, homosalate, amiloxate, octocrylene, ensulizole, diethylhexyl butamido triazone, polysilicone 15, padimate O, methylbenzylidene camphor, and combinations thereof. In some cases, the UVB absorber is selected from the group consisting of octinoxate, octocrylene, diethylhexyl butamido triazone, octyltriazone, and combinations thereof. For example, the UVB absorber can be octinoxate, octocrylene, or a combination thereof.

In some embodiments, the UVA absorber is avobenzone and the UVB absorber is octinoxate, octocrylene, or a combination thereof.

The solid material can be selected from the group consisting of acrylate nano latex, fumed silica, cetyl silica silylate, zeolite, natural clay, synthetic clay, ethyl cellulose, microcrystalline cellulose, cyclodextrin, vegetable protein, sodium caseinate, inulin lauryl carbamate, sodium octenylsuccinate starch, sodium octenylsuccinate phytoglycogen, and combinations thereof. In some cases, the solid material is selected from the group consisting of sodium magnesium silicate, fumed silica, cetyl silica silylate, lithium magnesium sodium silicate and combinations thereof. In various cases, the solid material is part of a complex comprising a cationic material selected from the group consisting of cetyl trimonium chloride, polyquaternium-59, methoxy cinnamidopropyl laurdimonium, methoxycinnamidopropyl hydroxy sultaine, dimethylpabamidopropyl laurdimonium tosylate, and combinations thereof.

The solid material can further include an emulsion stabilizing, water-soluble, surface active polymer, which can have a molecular weight greater than about 1000 Daltons and a surface tension in a range from about 15 nM/m to about 60 nM/m at 0.1 wt. % at 25° C. The surface active polymer can be selected from the group consisting of mono alkyl esters of poly(methyl vinyl ether/maleic acid) sodium salt and alkylated polyvinylpyrrolidone; terephthalate polyesters; and combinations thereof. In some embodiments, the surface active polymer is selected form the group consisting of butylated polyvinylpyrrolidone; monobutyl ethylester of poly(methyl vinyl ether/maleic acid) copolymer, sodium salt; and combinations thereof.

The dispersion can optionally include a humectant. The humectant can be selected from the group consisting of glycerin, 1,2-butylene glycol, propanediol, sorbitol, and combinations thereof.

The dispersion can optionally include a thickener. The thickener can be, for example, an ammonium or sodium acryloyldimethyltaurate/vp copolymer.

The dispersion can optionally include a chelating agent. The chelating agent can be, for example, sodium phytate, sodium polyitaconate itaconix, glutamic acid, N,N-diacetic acid-47% solids, trisodium ethylenediamine disuccinate-30% solids, trisodium methylglycinediacetate-86% solids, disodium ethylenediaminetetraacetic acid (EDTA), and combinations thereof.

The composition can optionally include a surfactant having an HLB value in a range of about 2 to about 6. In some cases, the surfactant is selected from group consisting of a sorbitan ester, a polyglyceryl ester, an ethoxylated fatty alcohol, a fatty acid, an ethoxylated fatty acid ester, lecithin, and combinations thereof. For example, the surfactant can be selected from the group consisting of polyglyceryl-6 polyricinoleate, polyglyceryl-2 dipolyhydroxystearate, lecithin, sorbitan oleate, and combinations thereof.

The dispersion can both absorb and scatter UV irradiation.

In some embodiments, the dispersion exhibits an in vivo SPF efficiency of at least about 6, or 8 m or 10, or 15, or 20 SPF units per 1 wt. % sunscreen.

In some cases, the discrete oil particles remain discrete for at least about 4 hours, or at least about 8 hours, after contact with a surface.

In various cases, the oil-in-water dispersion is stable at −15° C. for three freeze-thaw cycles and at 45° C. for one month, characterized by: (i) maintaining at least 95% of its chemical activity, or (ii) maintaining at least 95% of its SPF value, or (iii) exhibiting no crystallization, or (iv) exhibiting no change in physical appearance.

In some embodiments, the composition further comprises an aqueous sunscreen base. In these embodiments, the dispersion can be present in the composition in an amount in a range from about 1 wt. % to about 25 wt. %, or about 5 wt. % to about 20 wt. %, based on the total weight of the composition. The aqueous sunscreen base can be a hydrogel, an oil-in-water emulsion, or a water-in-oil emulsion.

In some embodiments, the aqueous sunscreen base is oil-in-water emulsion or a water-in-oil emulsion.

In various embodiments, the aqueous sunscreen base is a hydrogel. In these embodiments, the hydrogel can include a gelling agent. The gelling agent can be selected from the group consisting of crosslinked acrylate, crosslinked acrylic acid, crosslinked polyvinylpyrrolidone (PVP), polyimide-3, and combinations thereof. In some cases, the gelling agent is selected from the group consisting of acrylates/C10-30 alkyl acrylate crosspolymer, ammonium or sodium acryloyldimethyltaurate/vp copolymer, hydroxyethylacrylate/sodium acryloyldimethyltaurate copolymer, crosslinked polyvinylpyrrolidone, and combinations thereof. For example, the gelling agent can be sodium or ammonium acryloyldimethyltaurate/vinylpyrrolidone (VP) copolymer.

In various cases, the aqueous base is free of a photo stabilizer. In some embodiments, the aqueous base further includes a photo stabilizer.

In various embodiments, the aqueous base is free of a metal oxide.

The sunscreen composition can optionally include an additive selected from the group consisting of a preservative, a SPF booster, a waterproofing polymer, an emollient, a powder, a fragrance, a chelating agent, and combinations thereof.

Yet another aspect of the disclosure is a kit that includes first and second oil-in-water dispersions; each oil-in-water dispersion comprising an oil phase comprising discrete oil particles, each oil particle coated with a solid material. The oil particles in the first dispersion include an organic UVA absorber present in an amount in a range from about 10 wt. % to about 100 wt. %, based on the total weight of the oil particles in the first dispersion, and are free of a UVB absorber. The oil particles in the second dispersion include an organic UVB absorber present in an amount in a range from about 30 wt. % to about 100 wt. %, based on the total weight of the oil particles in the second dispersion, and are free of a UVA absorber. Each oil-in-water dispersion is free of a metal oxide, and the oil particles in each of the first and second oil-in-water dispersions are present in an amount in a range from about 50 wt. % to about 80 wt. %, based on the total weight of each of the first and second oil-in-water dispersions.

In some embodiments, the kit includes a UVA absorber selected from the group consisting of avobenzone, oxybenzone, bemotrizinol, diethylamino hydroxybenzoyl methyl benzoate, and combinations thereof. For example, the UVA absorber can be avobenzone. In various embodiments, the kit includes a UVB absorber selected from the group consisting of enzacamene, oxybenzone, octinoxate, octisalate, octyltriazone, homosalate, amiloxate, octocrylene, ensulizole, diethylhexyl butamido triazone, polysilicone 15, padimate O, methylbenzylidene camphor, and combinations thereof. For example, the UVB absorber can be octinoxate. In some cases, the oil particles in the first dispersion further comprise a photo stabilizer. The photo stabilizer can be selected from the group consisting of octocrylene, diethylhexyl naphthalate, undecylcrylene dimethicone, ethyl hexyl methoxycrylene, polyester-8, polyester 25, trimethoxybenzylidene pentanedione, diethylhexyl syringlidene malonate, tetramethyl hydroxy piperidinol, benzotriazole dodecyl p-cresol, sodium benzotriazole butyl phenol sulfonate, and combinations thereof. For example, the photo stabilizer can be octocrylene. In some exemplary embodiments, the oil particles in the first dispersion are composed of avobenzone and octocrylene, and the oil particles in the second dispersion are composed of octinoxate.

Still another aspect of the disclosure relates to a method of reducing contact of UV radiation on a surface comprising coating the surface with the composition described herein.

Yet another aspect of the disclosure provides a method of photostabilizing interactive UVA and UVB absorbers by maintaining them separated as discrete particles in the process of manufacture. In this method, a first oil-in-water dispersion containing an oil particle comprising an organic UVA absorber coated with a solid material is formed. Then, a second oil-in-water dispersion containing an oil particle comprising an organic UVB absorber coated with a solid material is formed. The first oil-in-water dispersion and the second oil-in-water dispersion are combined in an aqueous base, and the UVA and UVB oil particles from the first and second oil-in-water dispersions are maintained as discrete particles.

Further aspects and advantages will be apparent to those of ordinary skill in the art from a review of the following detailed description, taken in conjunction with the drawings. While the inhibitors and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION

Figure 1A:
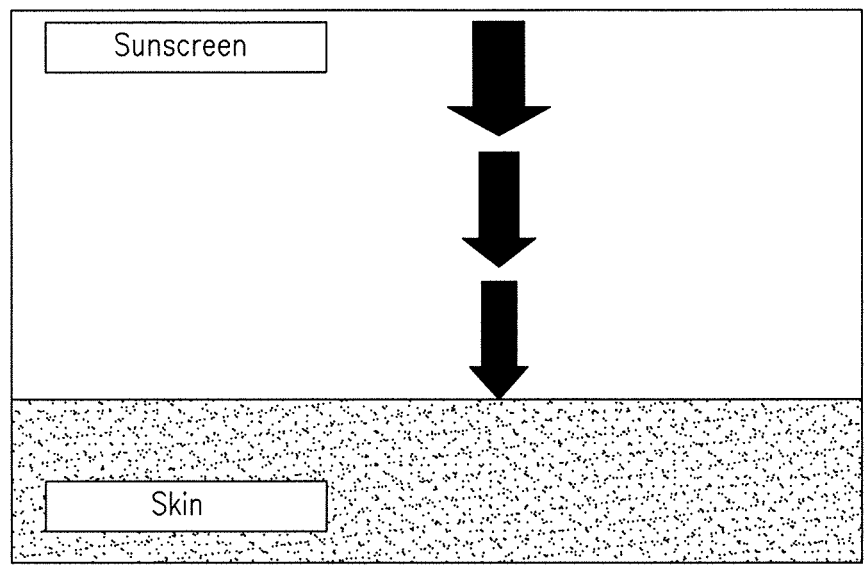
FIG. 1 is a schematic illustration comparing the performance of conventional sunscreen compositions (A) which only absorb UV light to the performance of sunscreen compositions in accordance with embodiments of the disclosure (B), which are able to both absorb and scatter UV light.

Disclosed herein are sunscreen compositions containing oil-in-water dispersions that include an oil phase composed of discrete oil particles that are coated with a solid material and dispersed in an aqueous phase. The sunscreen compositions can exhibit surprisingly high in vivo sun protection factor (SPF) efficiency due to their ability to both absorb and scatter ultraviolet (UV) light (FIG. 1).

In various embodiments, the dispersion includes first and second discrete oil particles, in which the first oil particles include an organic ultraviolet A (UVA) absorber and are free of a ultraviolet B (UVB) absorber, and the second oil particles include an organic UVB absorber and are free of a UVA absorber. The oil particles in such embodiments can optionally be free of a photo stabilizer. Without being bound by any particular theory, it is believed that separating the organic UVA and UVB absorbers from each other in discrete, oil particles that are unable to coalesce can prevent the UVA and UVB absorbers from interacting with, and thus, destabilizing each other. The separation of the UVA and UVB absorbers from each other also allows the UVB absorber to act as a shield to protect a photounstable UVA absorber from UV radiation, further stabilizing the composition. In some cases, the first discrete oil particles consist essentially of a UVA absorber. In these cases, the first discrete oil particles can optionally include, for example, a solvent or a photostabilizer (e.g., octocrylene). In various cases, the first discrete oil particles consist of a UVA absorber. In some embodiments, the second discrete oil particles consist essentially of a UVB absorber. In these cases, the second discrete oil particles can optionally include, for example, a solvent or a photostabilizer. In various cases, the second discrete oil particles consist of a UVB absorber. In some embodiments, each discrete, enclosed oil particle described here consists of a UVA absorber or a UVB absorber. In various embodiments, each discrete, enclosed oil particle consists essentially of or consists of a UVA absorber or a UVB absorber.

In accordance with other embodiments of the disclosure, the dispersion includes oil particles having a UVA absorbing compound and a UVB absorbing compound. In some such embodiments, the UVB compound can be present in an amount sufficient to absorb UVB radiation and also to stabilize the UVA absorbing compound. Examples of UVB absorbers that also stabilize UVA absorbing compounds include octocrylene, oxybenzone, methylbenzylidene camphor, and combinations thereof. In other embodiments, the oil particles can further include a photostabilizer.

The dispersions in accordance with various embodiments are stable at −15° C. for at least three freeze-thaw cycles and at 45° C. for at least 1 month. As used herein, the term "stable" refers to a dispersion that maintains at least 95% (e.g., 96%, 97%, 98%, 99%, or 100%) of its chemical activity and/or SPF value during the specified time period, or that exhibits no crystallization or change in its physical appearance during the specified time period. Therefore, the dispersions disclosed herein are shelf stable and shipping stable. In some embodiments, the dispersion maintains at least 95% of its chemical activity and SPF activity during the specified time period, and also exhibits no crystallization or change in its physical appearance during that time.

Figure 1B:
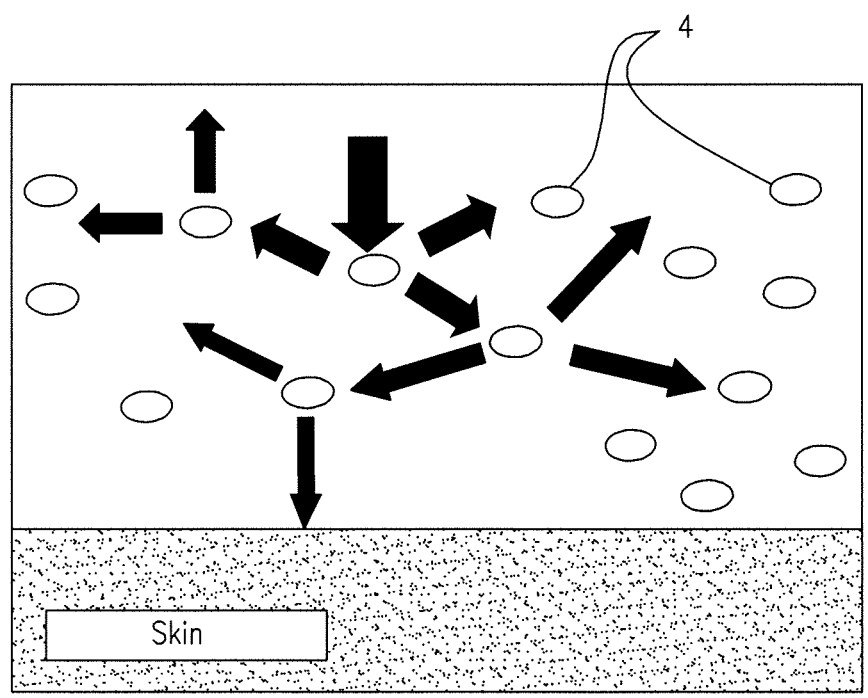

It has been advantageously found that coating the oil droplets containing the UV absorbers with a solid material can lead to improved in vivo SPF efficiency and photostability of the compositions that contain them. Without intending to be bound by theory, it is believed that the solid coating surrounding the oil particles aids in preventing breakage of the particles, coalescence of the particles, or other modification of the particles, which can result in release of the UV absorbers to directly contact with and potentially penetrate into the skin, and to migrate over the skin with time. This reduced penetration of the absorbers is particularly beneficial when the dispersions are prepared as sunscreen compositions for daily use. It has also been advantageously found that high concentrations of oil particles can be stably maintained in the dispersions in accordance with embodiments of the disclosure. Without being bound by any particular theory, it is believed that the enhanced performance of the dispersions results from the ability of the particles to stack on top of each other, particularly when the particles are highly concentrated in the dispersion, when applied to a surface, such as skin. Such stacking increases the film thickness, which correspondingly increases the optical path length that UV needs to travel through to the underlying surface. Furthermore, it has been found that the solid coating surrounding the oil particles can scatter UV light from the particle, thereby allowing the dispersions to both scatter and absorb light as illustrated in FIG. 1B. The combination of this light scattering ability, the enhanced UV absorbing ability of the particles, and their increased photostability results in compositions that exhibit unexpectedly and exceptionally high in vivo SPF efficiency. The solid coating enclosing the UVA and UVB absorbers also functions to prevent the absorbers from penetrating a user's skin and migrating over time.

As shown in the Examples section, below, the high efficiency sunscreen compositions disclosed herein include low concentrations of the UVA and UVB absorbers (e.g., 0.5 to 2 wt. % UVA absorber and 2.0 to 4.5 wt. % UVB absorber, based on the total weight of the composition), while exhibiting high in vivo SPF values (e.g., SPF 30), and excellent in vivo SPF efficiency (e.g., 7-13 SPF units per 1% sunscreen). See, e.g., Example E and Table 4, below. As a comparison, a conventional sunscreen composition having the same concentration of UVA and UVB absorbers would only exhibit an SPF 5. And, this conventional sunscreen composition would require about 19 wt. % of the UV absorbers to achieve an SPF 30. Furthermore, control sunscreen compositions having UV absorber concentrations of: (1) 3 wt. % UVA absorber and 7 wt. % UVB absorber and (2) 7 wt. % UVA absorber and 7.1 wt. % UVB absorber, only exhibited SPF values of 17 and 10, respectively. As previously described, it is believed that the highly concentrated oil particles of the dispersions disclosed herein stack on top of each other, which increases film thickness and the optical path length that UV needs to travel through to the underlying surface. Accordingly, the sunscreen compositions disclosed herein advantageously do not need as high an amount of UV absorber that conventional sunscreen compositions require to achieve similar SPF values.

Therefore, the sunscreen compositions disclosed herein are highly efficient, exhibiting an in vivo SPF efficiency of at least 6 SPF units per 1 wt. % of the sunscreen composition. As used herein, "SPF efficiency" refers to the ratio of the sun protection factor, or SPF, over the total wt. % of sunscreen actives, based on the total weight of the sunscreen composition. At such an efficiency, the sunscreen compositions described herein can achieve SPF 50 using less than 6 wt. % of UVA and UVB absorbers, and SPF 30 using less than 4 wt. % of UVA and UVB absorbers, based on the total weight of the composition. In some embodiments, the sunscreen compositions disclosed herein exhibit an in vivo SPF efficiency of at least 8 SPF units per 1 wt. % of the sunscreen composition, 10 SPF units per 1 wt. % of the sunscreen composition, or at least 13 SPF units per 1 wt. % of the sunscreen composition, or at least 15 SPF units per 1 wt. % of the sunscreen composition, or at least 17 SPF units per 1 wt. % of the sunscreen composition, or at least 20 SPF units per 1 wt. % of the sunscreen composition.

Oil-In-Water Dispersions

As discussed above, the sunscreen compositions disclosed herein include oil-in-water dispersions that are composed of discrete oil particles that are surrounded by a solid coating. The solid coating can optionally include a surface active polymer. The dispersions described herein can be free of a metal oxide (e.g., titanium dioxide or zinc oxide), such as a microfine metal oxide. Further, the dispersions can optionally include one or more excipients, such as humectants, thickeners, chelating agents, surfactants having a low hydrophobic-lipophilic balance (HLB), and combinations thereof.

The discrete oil particles are present in the dispersion at high concentrations. It is believed that high concentrations of the discrete particles in the dispersion can allow for enhanced ability of the particles to stack on each other when applied, and thereby improve the overall absorption behavior. In accordance with embodiments of the disclosure, the discrete oil particles can be present in the dispersion in an amount having a range from about 50 wt. % to about 80 wt. %, or about 50 wt. % to about 70 wt. %, or about 50 wt. % to about 60 wt. %, based on the total weight of the dispersion. For example, the discrete oil particles can be present in the dispersion in an amount of about 50 wt. %, or about 55 wt. %, or about 60 wt. %, or about 65 wt. %, or about 70 wt. %, or about 75 wt. %, or about 80 wt. %, based on the total weight of the dispersion.

The discrete oil particles have a particle size small enough to ensure sufficient UV light scattering ability. Accordingly, the discrete oil particles each can have a particle size (i.e., diameter) in a range from about 0.5 µm to about 200 µm, or about 0.5 µm to about 100 µm, or about 1 µm to about 150 µm, or about 5 µm to about 100 µm, or about 1 µm to about 10 µm, or about 0.5 µm to about 10 µm. For example, the discrete oil particles disclosed herein can have a particle size of about 0.5 µm, or about 0.6 µm, or about 0.7 µm, or about 0.8 µm, or about 0.9 µm, or about 1 µm, or about 2 µm, or about 3 µm, or about 4 µm, or about 5 µm, or about 6 µm, or about 7 µm, or about 8 µm, or about 9 µm, or about 10 µm, or about 11 µm, or about 12 µm, or about 13 µm, or about 14 µm, or about 15 µm, or about 16 µm, or about 17 µm, or about 18 µm, or about 19 µm, or about 20 µm, or about 21 µm, or about 22 µm, or about 23 µm, or about 24 µm, or about 25 µm, or about 26 µm, or about 27 µm, or about 28 µm, or about 29 µm, or about 30 µm, or about 31 µm, or about 32 µm, or about 33 µm, or about 34 µm, or about 35 µm, or about 36 µm, or about 37 µm, or about 38 µm, or about 39 µm, or about 40 µm.

For dispersions in accordance with embodiments of the disclosure, it has been found that the discrete oil particles can remain intact for at least about 4 hours, or at least about 5 hours, or at least about 6 hours, or at least about 7 hours, or at least about 8 hours, or at least about 9 hours, or at least about 10 hours, for example, up to about 12 hours, after application to a surface, such as a user's skin. The robustness of the oil particles prevents the particles from coalescing, which prevents the UVA and UVB absorbers from penetrating into a user's skin, and/or migrating across the skin over time. In embodiments when the UVA and UVB absorbers are separately enclosed within the oil particles, the robustness of the particles prevents the UVA and UVB absorbers from interacting with each other, causing destabilization.

The solid material coating the discrete oil particles can include, for example, acrylate nano latex, fumed silica (e.g., AEROSIL 300 by Evonik), cetyl silica silylate (e.g. AEROSIL R816 by Evonik), zeolite, natural clay, synthetic clay (e.g., LAPONITE XLG by BYK), ethyl cellulose (e.g., AQUACOAT ECD by FMC Biopolymer), microcrystalline cellulose, cyclodextrin (e.g., alpha cyclodextrin, beta cyclodextrin, or hydroxypropyl beta cyclodextrin), vegetable protein (SOBIND HARMONY SOPRANO by DuPont), sodium caseinate (e.g., EXCELLION EM 6 by DMV International), inulin lauryl carbamate (e.g. INUTEC SP1 by Orafti), sodium octenylsuccinate starch (PURITY GUM ULTRA by Ingredion), sodium octenylsuccinate phytoglycogen, and combinations thereof. Using, for example, acrylate-based latex or ethyl cellulose as the solid material can be advantageous because these solids are similar in polarity to many sunscreen ingredients and solubilizers, which allows the sunscreen ingredients to plasticize the particle on the oil droplet after emulsification, resulting in a film surrounding the droplet. This film allows the droplet to exhibit improved emulsion stability and UV scattering. In some embodiments, the solid coating includes sodium magnesium silicate, fumed silica, cetyl silica silylate, lithium magnesium sodium silicate and combinations thereof. In various cases, the solid coating can further include a complex of a cationic material and a compound selected from the group consisting of sodium magnesium silicate, colloidal silica, fumed silica, lithium magnesium sodium silicate, and combinations thereof. In these embodiments, the cationic material can be selected from the group consisting of cetyl trimonium chloride, polyquatemium-59, methoxy cinnamidopropyl laurdimonium, methoxycinnamidopropyl hydroxy sultaine, dimethylpabamidopropyl laurdimonium tosylate, and combinatons thereof. In some cases, the solid coating can include butylated polyvinylpyrrolidone (PVP), monobutyl ethylester poly(methyl vinyl ether/maleic acid) copolymer sodium salt, and combinations thereof. Commercially available examples of the solid coating include, but are not limited to EASTMAN AQ 38 (polyester 5, by Eastman-Chemical), AQUACOAT ECD (ethyl cellulose, 20-30% ethyl cellulose latex dispersion by FMC), SOBIND HARMONY SOPRANO (glycine soja (soybean) protein oil by DuPont), LAPONITE XLG (by Byk), PURITY GUM ULTRA (sodium octenylsuccinate starch by Ingredion), and combinations thereof. In some embodiments, the solid material can be present in a range from about 1.0 wt. % to about 10 wt. %, based on the total weight of the dispersion. In some embodiments, the solid material is present in a range from about 1.0 wt. % to about 7 wt. %, or about 1.0 wt. % to about 5 wt. %, based on the total weight of the dispersion, or in an amount of about 1 wt. %, or about 2 wt. %, or about 3 wt. %, or about 4 wt. %, or about 5 wt. %, or about 6 wt. %, or about 7 wt. %, based on the total weight of the dispersion.

The solid coating can include an emulsion-stabilizing, water-soluble, surface active polymer. The surface active polymer can have a molecular weight greater than about 1000 Daltons, and a surface tension in a range from about 15 nM/m to about 60 nM/m at about 0.1 wt. % in water at 25° C. In some embodiments, the surface active polymer has a molecular weight up to about 50K Daltons, and a surface tension in a range from about 40 nM/m to about 60 nM/m at about 0.1 wt. %, based on the total weight of the polymer in water. The surface active polymer can be selected from the group consisting of mono alkyl esters of poly(methyl vinyl ether/maleic acid) sodium salt and alkylated polyvinylpyrrolidone; terephthalate polyesters; and combinations thereof. For example, the surface active polymer can be selected from the group consisting of butylated polyvinylpyrrolidone (GANEX 904 by Ashland); monobutyl ethylester of poly(methyl vinyl ether/maleic acid) copolymer, sodium salt (EASY-SPERSE P20 by Ashland); and combinations thereof. The surface active polymer can be present in an amount in a range from about 0.5 wt. % to about 2 wt. %, based on the total weight of the dispersion. For example, the surface active polymer can be present in an amount in a range from about 0.5 wt. %, or about 0.6 wt. %, or about 0.7 wt. %, or about 0.8 wt. %, or about 0.9 wt. %, or about 1.0 wt. %, or about 1.1 wt. %, or about 1.2 wt. %, or about 1.3 wt. %, or about 1.4 wt. %, or about 1.5 wt. %, or about 1.6 wt. %, or about 1.7 wt. %, or about 1.8 wt. %, or about 1.9 wt. %, or about 2.0 wt. %, based on the total weight of the dispersion.

In some embodiments, each of the discrete, enclosed oil particles described herein is composed of either a UVA absorber or a UVB absorber, but not both. In various embodiments, each of the discrete, enclosed oil particles described herein contains a UVA absorber, a UVB absorber, and a photostabilizer. In some cases, the UVB absorber also functions as the photostabilizer. Examples of UVB absorbers that also stabilize UVA absorbers include octocrylene, oxybenzone, methylbenzylidene camphor, and combinations thereof. The some embodiments, each of the discrete, enclosed oil particles described herein consist essentially of either a UVA absorber or a UVB absorber. In these embodiments, each discrete, enclosed oil particle can optionally include a solvent and/or a photo stabilizer. In various embodiments, each discrete, enclosed oil particle described here consists of a UVA absorber or a UVB absorber. In various embodiments, each discrete, enclosed oil particle consists essentially of or consists of a UVA absorber or a UVB absorber.

The UVA absorber can be any oil-soluble, organic compound that absorbs UVA radiation. Suitable UVA absorbers include bemotrizinol, avobenzone, bisdisulizole disodium, meradimate, bisoctotrizole, ecamisule, diethylamino hydroxybenzoyl methyl benzoate, drometrizole trisiloxane and combinations thereof. In some embodiments, the UVA absorber is selected from the group consisting of avobenzone, bemotrizinol, diethylamino hydroxybenzoyl methyl benzoate, and combinations thereof. For example, the UVA absorber can be avobenzone. In accordance with embodiments when the UVA absorber and UVB absorber are present together in the same discrete oil particles, the UVA absorber can be present in the oil particles in an amount in a range from about 10 wt. % to about 70 wt. %, or about 20 wt. % to about 70 wt. %, or about 30 wt. % to about 70 wt. %, or about 40 wt. % to about 70 wt. %, or about 50 wt. % to about 70 wt. %, based on the total weight of the oil particle. In accordance with embodiments when the dispersion includes first and second discrete oil particles, in which the first oil particles include a UVA absorber and the second oil particles includes a UVB absorber, the UVA absorber can be present in the first oil particles in an amount in a range from about 10 wt. % to about 100 wt. %, or about 20 wt. % to about 100 wt. %, or about 30 wt. % to about 100 wt. %, or about 40 wt. % to about 100 wt. %, or about 50 wt. % to about 100 wt. %, based on the total weight of the first oil particles.

The UVB absorber can be any oil-soluble, organic compound that absorbs UVB radiation. Suitable UVB absorbers include enzacamene, oxybenzone, octinoxate, octisalate, octyltriazone, homosalate, amiloxate, octocrylene, ensulizole, diethylhexyl butamido triazone, polysilicone 15, padimate O, methylbenzylidene camphor, and combinations thereof. In some embodiments the UVB absorber is selected from the group consisting of octinoxate, oxybenzone, octocrylene, diethylhexyl butamido triazone, octyltriazone, and combinations thereof. For example, the UVB absorber can be octinoxate, octocrylene, or both. In some embodiments, the UVB absorber is octinoxate. In accordance with embodiments when the UVB absorber can also stabilize the UVA absorber, the UVB absorber can be selected from the group consisting of octocrylene, oxybenzone, methylbenzylidene camphor, and combinations thereof. For example, the UVB absorber can be octocrylene. In accordance with embodiments when the UVA absorber and UVB absorber are present together in the same discrete oil particles, the UVB absorber can be present in the oil particles in an amount in a range from about 30 wt. % to about 90 wt. %, or about 40 wt. % to about 90 wt. %, or about 50 wt. % to about 90 wt. %, or about 60 wt. % to about 90 wt. %, or about 70 wt. % to about 90 wt. %, or about 80 wt. % to about 90 wt. %, based on the total weight of the oil particle. In accordance with embodiments when the dispersion includes first and second discrete oil particles, in which the first oil particles include a UVA absorber and the second oil particles includes a UVB absorber, the UVB absorber can be present in the second oil particles in an amount in a range from about 30 wt. % to about 100 wt. %, or about 40 wt. % to about 100 wt. %, or about 50 wt. % to about 100 wt. %, or about 60 wt. % to about 100 wt. %, or about 70 wt. % to about 100 wt. %, or about 80 wt. % to about 100 wt. %, or about 90 wt. % to about 100 wt. %, based on the total weight of the first oil particles.

In some cases, the UVA absorber is avobenzone and the UVB absorber is octinoxate, octocrylene, or a combination thereof. In some embodiments, the UVA absorber is avobenzone present in an amount of about 10 wt. % to about 30 wt. %, and the UVB absorber is octinoxate present in an amount of about 50 wt. % to about 70 wt. %, based on the total weight of the dispersion. In various embodiments, the UVA absorber is avobenzone present in an amount of about 10 wt. % to about 15 wt. %, and the UVB absorber is octocrylene present in an amount of about 15 wt. % to about 35 wt. %. In various cases, the UVA absorber is avobenzone present in an amount of about 15 wt. % to about 20 wt. %, and the UVB absorber includes octinoxate present in an amount of about 50 wt. % to about 60 wt. % and octocrylene present in an amount of about 30 wt. % to about 35 wt. %.

In some embodiments, the oil-soluble UVA and/or UVB absorber is a liquid. In these embodiments, the UVA and/or UVB absorber can be enclosed in discrete oil particles without prior solubilization. In accordance with these embodiments, the UV absorber can be present in an amount ranging from about 30 wt. % to about 60 wt. %, or about 40 wt. % to about 50 wt. %, based on the total weight of the dispersion. For example, the liquid UV absorber can be present in an amount of about 30 wt. %, or about 35 wt. %, or about 40 wt. %, or about 45 wt. %, or about 50 wt. %, or about 55 wt. %, or about 60 wt. %, based on the total weight of the dispersion.

In other embodiments, the UVA and/or UVB absorber is crystalline. In these embodiments, the UVA and/or UVB absorber is dissolved in a solvent before enclosure in a discrete oil particle through emulsification. The solvent into which the UVA and/or UVB absorber is dissolved can be any solvent that dissolves at least about 10% of the crystalline UVA and/or UVB absorber, but that is not water soluble itself. Suitable solvents include, but are not limited to $C_{12-15}$ alcohol benzoate (e.g., FINSOLV TN by InnoSpec), ethylhexyl benzoate (e.g., FINSOLVE EB by InnoSpec), dipropylene glycol dibenzoate (e.g., FINSOLV PG22 by InnoSpec), butylphthalimide isopropylphthalimide (e.g., PELEMOL PIP by Phoenix Chemical), phenyl ethyl benzoate (e.g., X-TEND 226 by Ashland), dioctyl isosorbide, dioctyl maleate (BERNEL ESTER DOM by Alzo), phenoxycaprylate, isopropyl lauryl sarcosinate (e.g., ELDEW SL 205 BY Ajinomoto), ethyl hexyl methoxycrylene (e.g., SOLASTAY 51 by HallStar), neopentyl glycol dipeptanoate (LEXFEEL 7 by Inolex), and combinations thereof. In accordance with these embodiments, the UV absorber can be present in an amount ranging from about 1 wt. % to about 25 wt. %, or from about 2 wt. % to about 20 wt. %, or from about 5 wt. % to about 10 wt. %, based on the total weight of the dispersion. For example, the crystalline UV absorber can be present in an amount of about 1 wt. %, or about 2 wt. %, or about 3 wt. %, or about 4 wt. %, or about 5 wt. %, or about 6 wt. %, or about 7 wt. %, or about 8 wt. %, or about 9 wt. %, or about 10 wt. %, or about 11 wt. %, or about 12 wt. %, or about 13 wt. %, or about 14 wt. %, or about 15 wt. %, or about 16 wt. %, or about 17 wt. %, or about 18 wt. %, or about 19 wt. %, or about 20 wt. %, based on the total weight of the dispersion. In these embodiments, the solvent into which the crystalline UV absorber is dissolved can be present in an amount from about 20 wt. % to about 50 wt. %, based on the total weight of the dispersion. For example, the solvent can be present in an amount of about 20 wt. %, or about 25 wt. %, or about 30 wt. %, or about 35 wt. %, or about 40 wt. %, or about 45 wt. %, or about 50 wt. %, based on the total weight of the dispersion. In some embodiments, waxes can be used as solvents to dissolve crystalline UVA and/or UVB absorbers at elevated temperatures. In these embodiments, the UVA and/or UVB absorbers are emulsified using high shear homogenization and then rapidly cooled to form non-crystalline particles.

In some embodiments, the UVA absorber is crystalline and the UVB absorber is a liquid.

The photostabilizer can include any compound that reduces the chemical reactivity of a UV absorber, such as the UVA absorber. Suitable photo stabilizers include, for example, diethylhexyl naphthalate (CORAPAN TQ by Symrise), undecylcrylene dimethicone (HALLBRITE PSF by Hallstar), ethyl hexyl methoxycrylene (SOLASTAY S1 by Hallstar), polyester-8 (POLYCRYLENE Si by Hallstar), polyester 25 (SOLASTAY P1 by Hallstar), trimethoxybenzylidene pentanedione (SYNOXYL HSS by Sytheon), diethylhexyl syringlidene malonate (OXYNEX ST LIQUID by EMD), tetramethyl hydroxy piperidinol (TINOGARD Q by BASF), benzotriazole dodecyl p-cresol (TINOGARD TS by BASF), sodium benzotriazole butyl phenol sulfonate (TINOGARD HS by BASF), and combinations thereof. In some cases, the photostabilizer also can absorb UVB irradiation. Examples, of UVB absorbers that act as photostabilzers include octocrylene, oxybenzone, and methylbenzylidene camphor. In some embodiments, the photostabilizer is selected from the group consisting of octocrylene, diethylhexyl naphthalate, undecylcrylene dimethicone, ethyl hexyl methoxycrylene, polyester-8, polyester 25, trimethoxybenzylidene pentanedione, diethylhexyl syringlidene malonate, tetramethyl hydroxy piperidinol, benzotriazole dodecyl p-cresol, sodium benzotriazole butyl phenol sulfonate, and combinations thereof. In various embodiments, the photostabilizer is selected from the group consisting of octocrylene, diethylhexyl naphthalate, ethyl hexyl methoxycrylene, and combinations thereof. For example, the photostabilizer can be octocrylene. The photostabilizer can be present in the dispersion in an amount in a range of about 0.1 wt. % to about 20 wt. %, or about 1 wt. % to about 10 wt. %, or 10 wt. % to about 20 wt. %, or about 0.5 wt. % to about 5 wt. %, or about 5 wt. % to about 15 wt. %.

In embodiments wherein the discrete oil particles include both a UVA absorber and a UVB absorber, and when one absorber has a high polarity (e.g., the UVB absorber is octocrylene), then an excipient having a lower dielectric constant (e.g., diethylhexyl naphthalate, octinoxate, homosalate, butylphthalimide isopropylphthalimide, dipropylene glycol dibenzoate, and/or dioctyl maleate) can be added to the dispersion to prevent a decrease in SPF efficiency.

In some embodiments, the dispersions disclosed herein further include a humectant. The humectant can function to improve the stability (e.g., shelf stability) of the dispersion, such as during freeze/thaw cycles. Additionally or alternatively, the humectant can function to reduce the amount of preservative in the dispersion, e.g., to a level in a range of about 1 wt. % to about 20 wt. %. Suitable humectants include, but are not limited to glycerin, 1,2-butylene glycol, propanediol, sorbitol, and combinations thereof. The humectant can be present in the dispersion in an amount in a range of about 5 wt. % to about 20 wt. %, or about 5 wt. % to about 10 wt. %, or about 10 wt. % to about 15 wt. %, or about 15 wt. % to about 20 wt. %, or about 8 wt. % to about 15 wt. %.

In various cases, the dispersions disclosed herein further include a thickener. The thickener can function to improve the stability (e.g., shelf stability) of the dispersion, such as the heat stability of the dispersion. Suitable thickeners include, but are not limited to, swellable crosslinked polymers, such as crosslinked acrylate, crosslinked acrylic acid, crosslinked polyvinylpyrrolidone (PVP), polyamide-3, or combinations thereof. In some cases, the gelling agent is selected from the group consisting of acrylates/$C_{10-30}$ alkyl acrylate crosspolymer (e.g., CARBOPOL ULTREZ 21 polymer by Lubrizol), ammonium or sodium acryloyldimethyl-taurate/vp copolymer (ARISTOFLEX by Clairant), hydroxyethylacrylate/sodium acryloyldimethyltaurate copolymer, crosslinked polyvinylpyrrolidone (e.g., SEPINOV EMT 10 by Seppic), polyimide-3 resulting from the condensation of dilinoleic acid, ethylenediamine, polypropylene glycol diamine end-capped with PEG/PPG-32/10 aminopropyl methyl ether (OLEOCRAFT HP-31 by Hydresia), and combinations thereof. In some embodiments, the thickener includes ammonium or sodium acryloyldimethyltaurate/vinylpyrrolidone (VP) copolymer, such as ARISTOFLEX by Clairant. In some embodiments, the thickener can include ammonium acryloyldimethyltaurate/vp copolymer (ARISTOFLEX AVC by Clariant), sodium acryloyldimethyltaurate/vp copolymer (ARISTOFLEX AVS by Clariant), ammonium acryloyldimethyltaurate/beheneth-25 methacrylate crosspolymer (ARISTOFLEX HMB by Clairant), and combinations thereof. The thickener can be present in the dispersion in an amount in a range of about 0.05 wt. % to about 0.5 wt. %, or about 0.05 wt. % to about 0.1 wt. %, or about 0.3 wt. % to about 0.5 wt. %, or about 0.1 wt. % to about 0.4 wt. %, or about 0.05 wt. % to about 0.2 wt. %.

In various cases, the dispersions disclosed herein further include a chelating agent. The chelating agent can prevent interaction of a metal with UVA absorbers, such as avobenzone. Suitable chelating agents include, for example, sodium phytate (by Ankang Shi Mao Biotech), sodium polyitaconate itaconix (VELSOFT by Itaconix Corp.), glutamic acid, N,N-diacetic acid-47% solids (DISSOLVINE GL-47S by Akzo Nobel), trisodium ethylenediamine disuccinate-30% solids (NATRLQUEST E30 by Innospec), trisodium methylglycinediacetate-86% solids (TRILON M POWDER, by BASF), and disodium ethylenediaminetetraacetic acid (EDETA BD by BASF). The chelating agent can be present in the dispersion in an amount in a range of about 0.01 wt. % to about 0.1 wt. %, or about 0.01 wt. % to about 0.05 wt. %, or about 0.05 wt. % to about 0.1 wt. %, or about 0.08 wt. % to about 0.1 wt. %, or about 0.03 wt. % to about 0.07 wt. %.

In some embodiments, the premixes disclosed herein further include a low HLB surfactant (e.g., a surfactant having an HLB value in a range of about 2 to about 6). The low HLB surfactant can act as a co-stabilizer for the premix. Without being bound by any particular theory, the low HLB surfactant can reduce the surface tension of the oil droplet, which causes an increase in the contact angle of the solid coating at the oil interface. Because of the increase in contact angle, the solid coating can further embed itself into the oil droplet and it can also decrease the size of the discrete particle. Suitable low HLB surfactants include, for example, sorbitan esters (e.g., sorbitan oleate (HLB 4.3), sorbitan sequioleate, sorbitan isostearate (HLB 4.7), and sorbitan olivate (HLB 4.7)), polyglyceryl esters with a mono content in a range of about 30-60% (e.g., glyceryl oleate (40% mono content, HLB about 4), glyceryl isostearate (40% mono content, HLB 3.5), glyceryl ricinoleate, polyglyceryl-3 oleate, polyglyceryl-2 sesquioleate, polyglyceryl-3 pentaolivate, polyglyceryl-2 oleate, polyglyceryl-10 hexaoleate, polyglyceryl-10 decaoleate, polyglyceryl-3 isostearate, polyglyceryl-4 isostearate, polyglyceryl-2 sesquiisostearate, polyglyceryl-2 diisostearate, polyglyceryl-3 diisostearate, polyglyceryl-2 triisostearate, polyglyceryl-4 isostearate, polyglyceryl-3 ricinoleate, polyglyceryl-3 polyricinoleate, polyglyceryl-6 polyricinoleate, polyglyceryl-2 dipolyhydroxystearate, polyglyceryl-2 sesquicaprylate (HLB 8), and polyglyceryl-2 caprate), ethoxylated fatty alcohols (e.g., oleth 2 (HLB 5), oleth 3, isosteareth 2, and isosteareth 3), fatty acids (e.g., oleic (HLB 2), isostearic, ricinoleic, polyhydroxystearic, and polyricinoleic), Castor oil (e.g., PEG-7 hydrogenated castor oil, PEG 5 castor oil (HLB 3.9)), ethoxylated fatty acids (e.g., PEG-30 dipolyhydroxystearate), and lecithin. In some embodiments, the low HLB surfactant is selected from the group consisting of polyglyceryl-6 polyricinoleate, polyglyceryl-2 dipolyhydroxystearate, lecithin, sorbitan oleate, and combinations thereof. The low HLB surfactant can be present in the dispersion in an amount in a range of about 1 wt. % to about 20 wt. %, or about 2 wt. % to about 15 wt. %, or about 5 wt. % to about 10 wt. %, based on the total weight of the dispersion. In some embodiments, the UVA dispersion includes polyglyceryl 3 isostearate. In various embodiments, the UVB dispersion includes sorbitan oleate. In some cases, the UVA/UVB dispersion includes polyglyceryl-6 polyricinoleate.

Sunscreen Compositions

The compositions described herein that include oil-in-water dispersions composed of discrete oil particles surrounded by a solid coating can further include an aqueous sunscreen base. In some cases, a UVA only dispersion (which does not contain a UVB absorber) can be present in the composition in a range from about 2 wt. % to about 20.0 wt. %, based on the total weight of the sunscreen composition. For example, the UVA dispersion can be present in an amount of about 1 wt. %, or about 5 wt. %, or about 15 wt. %, or about 20 wt. %, based on the total weight of the composition. In various cases, a UVB only dispersion (which does not include a UVA absorber) can be present in the composition in a range from about 5 wt. % to about 15 wt. %, or about 5 wt. % to about 10 wt. %, based on the total weight of the composition. For example, the UVB dispersion can be present in an amount of about 5 wt. %, or about 6 wt. %, or about 7 wt. %, or about 8 wt. %, or about 9 wt. %, or about 10 wt. %, or about 11 wt. %, or about 12 wt. %, or about 13 wt. %, or about 14 wt. %, or about 15 wt. %, based on the total weight of the composition. In accordance with some embodiments, a UVA/UVB dispersion, optionally including a photostabilizer, can be present in the composition in a range from about 1 wt. % to about 25 wt. %, or about 5 wt. % to about 20 wt. %, or about 10 wt. % to about 15 wt. %, or about 2 wt. % to about 10 wt. %, or about 5 wt. % to about 15 wt. %, based on the total weight of the composition. For example, the UVA/UVB dispersion can be present in an amount of about 1 wt. %, or about 2 wt. %, or about 3 wt. %, or about 4 wt. %, or about 5 wt. %, or about 6 wt. %, or about 7 wt. %, or about 8 wt. %, or about 9 wt. %, or about 10 wt. %, or about 11 wt. %, or about 12 wt. %, or about 13 wt. %, or about 14 wt. %, or about 15 wt. %, or about 16 wt. %, or about 17 wt. %, or about 18 wt. %, or about 19 wt. %, or about 20 wt. %, or about 21 wt. %, or about 22 wt. %, or about 23 wt. %, or about 24 wt. %, or about 25 wt. %, based on the total weight of the composition.

These sunscreen compositions can include any combination of solid coating, optional surface active polymer, UVA absorber, UVB absorber, and aqueous base described herein, at any of the concentrations and particle sizes disclosed herein. In some embodiments, the sunscreen compositions described herein form continuous films when applied to skin, making them maximally effective.

Suitable aqueous sunscreen bases include hydrogels, oil-in-water emulsions, and water-in-oil emulsions. For example, sunscreen compositions that included an oil-in-water dispersion composed of octinoxate and avobenzone enclosed together in the same oil particles exhibited similar SPF values of about 33 when added to a hydrogel base (ARISTOFLEX AVC), an oil-in-water emulsion, or a water in silicone emulsion. The final amount of octinoxate and avobenzone in those compositions was 2 wt. % and 0.5 wt. %, respectively, based on the total weight of the compositions.

In some embodiments, the aqueous sunscreen base is an oil-in-water emulsion. In some cases, the aqueous sunscreen base is a water-in-oil emulsion.

In various embodiments, the aqueous sunscreen base is a hydrogel. In these embodiments, the base includes a gelling agent, such as a swellable crosslinked polymer. Suitable gelling agents include, but are not limited to, crosslinked acrylate, crosslinked acrylic acid, crosslinked polyvinylpyrrolidone (PVP), polyamide-3, or combinations thereof. In some cases, the gelling agent is selected from the group consisting of acrylates/$C_{10-30}$ alkyl acrylate crosspolymer (e.g., CARBOPOL ULTREZ 21 polymer by Lubrizol), ammonium or sodium acryloyldimethyltaurate/vp copolymer (ARISTOFLEX by Clairant), hydroxyethylacrylate/sodium acryloyldimethyltaurate copolymer, crosslinked polyvinylpyrrolidone (e.g., SEPINOV EMT 10 by Seppic), polyimide-3 resulting from the condensation of dilinoleic acid, ethylenediamine, polypropylene glycol diamine endcapped with PEG/PPG-32/10 aminopropyl methyl ether (OLEOCRAFT HP-31 by Hydresia), and combinations thereof. In some exemplary embodiments, the gelling agent includes ammonium or sodium acryloyldimethyltaurate/vinylpyrrolidone (VP) copolymer, such as ARISTOFLEX AVS by Clairant. The acryloyldimethyltaurate/VP copolymers have been found to significantly improve the in vivo SPF efficiency of sunscreen compositions. Without being bound by any particular theory, the initially swollen particles of the ammonium or sodium acryloyldimethyltaurate/vp copolymer gelling agent shrink when applied to a surface, such as a sunscreen user's skin, which helps to stabilize the enclosed, discrete oil particles and to keep them separate. In some embodiments, the gelling agent is present in the composition in a range from about 0.5 wt. % to about 2 wt. %, or about 1.0 wt. % to about 1.5 wt. %, based on the total weight of the sunscreen composition. For example, the gelling agent can be present in an amount of about 0.5 wt. %, or about 0.6 wt. %, or about 0.7 wt. %, or about 0.8 wt. %, or about 0.9 wt. %, or about 1.0 wt. %, or about 1.1 wt. %, or about 1.2 wt. %, or about 1.3 wt. %, or about 1.4 wt. %, or about 1.5 wt. %, based on the total weight of the dispersion.

In some exemplary embodiments, the high efficiency sunscreen compositions includes a dispersion with oil particles having a solid coating that includes a synthetic clay, such as LAPONITE LXG by BYK, and a butylated polyvinylpyrrolidone surface active polymer, such as GANEX 904 by Ashland and a gelled base containing an ammonium or sodium acryloyldimethyltaurate/vp copolymer, such as ARISTOFLEX by Clairant. In other exemplary embodiments, the sunscreen compositions includes a dispersion having a solid coating that includes a microcrystalline cellulose, such as AQUACOAT ECD by FMC Biopolymer and no surface active polymer, and a gelled base containing an ammonium or sodium acryloyldimethyltaurate/VP copolymer, such as ARISTOFLEX by Clairant. In some cases, the UVA and UVB absorbers can be present in the sunscreen composition in an amount of about 0.5 wt. % and 2 wt. %, respectively, based on the total weight of the sunscreen composition. The sunscreen compositions of these exemplary embodiments can exhibit an in vivo SPF efficiency of greater than about 20 SPF units per 1 wt. % of the sunscreen composition, such as 23 SPF units, 25 SPF units, 27 SPF units, 30 SPF units or 32 SPF units per 1 wt. % of the sunscreen composition.

The high efficiency sunscreen compositions can further include an additive. Suitable additives for inclusion in a sunscreen composition include, but are not limited to, SPF boosters, waterproofing agents, photostabilizers, preservatives, emulsifiers, emollients, powders, fragrances, chelating agents, and combinations thereof. The composition and concentration of these additives are well known to those skilled in the art.

In some cases, the high efficiency sunscreen composition can further include an SPF booster. The SPF booster can include any compound that improves the SPF index of a sunscreen formulation. Suitable SPF boosters include, but are not limited to, polyacrylate 15 and 17 (SYNTRAN PC 5227, 30% latex solids, by Interpolymer), water and hydrolyzed wheat protein/PVP crosspolymer (SOLPERFORM, 29% solids, by Croda), polyethylene (PERFORMALENE 400 by New Phase Technologies), tris(PPG-3 benzyl citrate) (CROMOLLIENT ESP by Croda), polyurethane 34 (BAYCUSAN C1000, 40% latex solids, by Bayer Material Science), sorbitol/sebacic acid copolymer behenate (SYNCROWAX ORM by Croda), styrene/acrylates copolymer (SUNSPHERES, 90% active powder, by Dow Chemical), acrylates copolymer (EPITEX 66, 45% solids in water, by Dow Chemical), $C_{28-52}$ olefin/undecylenic acid copolymer (PERFORMA V 6112 by New Phase Technologies), $C_{30-38}$ olefin isopropyl maleate/ma copolymer (PERFORMA V1608 by New Phase Technologies), eicosene/PVP (GANEX V220 by Ashland), tricontanyl/PVP (ANTARON/GANEX WP 660 by Ashland), and combinations thereof. The SPF booster can be present in the composition in an amount in a range of about 1 wt. % to about 10 wt. %, or about 1 wt. % to about 5 wt. %, based on the total weight of the composition. In some embodiments, the sunscreen composition includes avobenzone alone, octinoxate alone, or a combination of separately enclosed avobenzone and octinoxate as the UVA and UVB absorbers in a ratio of 1:0 to 1:3; AQUACOAT ECD or LAPONITE XLG combined with GANEX P904 as the solid coating material; and SUNSPHERES as the SPF booster.

In various embodiments, the high efficiency sunscreen composition can further include a waterproofing agent. The waterproofing agent can include any agent that increases the water-resistant properties of the sunscreen composition. Suitable waterproofing agents include, but are not limited to, acrylates/octylacrylamide copolymer (DERMACRYL LT, DERMACRYL 79, DERMACRYL 2.0 by Akzo Nobel), styrene/acrylates copolymer (DERMACRYL E bu Akzo Nobel), $C_{8-22}$ alkyl acrylate/methacrylate acid crosspolymer (INTELIMER 8600 EMULSION POLYMER by Air Products and Chemicals), $C_{10-30}$ alkyl acrylate (INTELIMER 13-1/13-6 POLYMER by Air Products), $C_{30-38}$ olefin isopropyl maleate/MA copolymer (PERFORMA V1608 (by New Phase Technologies), polyamide 3 (OLEOCRAFT HP 31, MP30, MP31 by Croda), polyamide 8 (OLEOCRAFT LP 20 by Croda), hydrogenated dimer dilinoleyl/dimethylcarbonate (COSMEDIA DC by BASF), Acrylates, $C_{12-22}$ alkyl methacrylate copolymer (ALLIANZ OPT by Dow Chemical; EPITEX 66 by Dow Chemical), polyvinyl stearate (GIOVAREZ 1800 by Phoenix Chemical), shellac (POLY-SOLEIL SY 400 by Mantrose-Haeuser), eicosene/PVP (GANEX V220 by Ashland), tricontanyl/PVP (ANTARON/GANEX wp 660 by Ashland), acrylates copolymer (EPITEX 66, 44.5% solids, by Dow Chemical) and combinations thereof. The waterproofing agent can be present in the composition in an amount in a range of about 1 wt. % to about 10 wt. %, or about 1 wt. % to about 5 wt. %, based on the total weight of the composition.

In some embodiments, the high efficiency sunscreen composition can further include a photostabilizer. Including a photostabilizer in the sunscreen composition can increase the composition's in vivo SPF efficiency at least 5 SPF units, or at least 7 SPF units, or at least 10 SPF units, or at least 20 SPF units per 1 wt. % of the sunscreen composition. The photostabilizer can include any compound that reduces the chemical reactivity of a UV absorber, such as the UVA absorber. Suitable photostabilizers were previously described herein. The photostabilizer can be present in the composition in an amount in a range of about 1 wt. % to about 10 wt. %, or about 1 wt. % to about 5 wt. %, or about 5 wt. % to about 10 wt. %, based on the total weight of the composition.

In some cases, the high efficiency sunscreen composition does not include a photostabilizer.

In some embodiments, the high efficiency sunscreen composition is free of a metal oxide (e.g., titanium dioxide or zinc oxide), such as a microfine metal oxide. In some cases, the high efficiency sunscreen composition includes a metal oxide, such as a microfine metal oxide as a component of the aqueous base.

In various cases, the high efficiency sunscreen composition does not include an emulsifier.

The sunscreen compositions described herein can be used for recreational and/or daily wear applications. Daily wear compositions are typically applied to a user's face, and therefore, should be non-greasy, non-irritating, and have good skin feel. Traditional daily wear sunscreen compositions, however, often require high concentrations of the UVA and UVB absorbers to achieve SPF values of 15 or 30, resulting in low in vivo SPF efficiencies (e.g., average efficiency about 2.5 SPF units per 1% sunscreen composition). Further, over time, the components in traditional daily wear compositions can migrate across and penetrate into the skin due to oil production, which can cause irritation. This problem is particularly troublesome when sunscreen compositions include high concentrations of absorbers, and also in compositions that include the UVA absorber stabilizer, oxybenzone, which is a known allergen and irritant.

Advantageously, the sunscreen compositions described herein are particularly suited for daily wear applications because they are effective at low UVA and UVB absorber concentrations and their oil particles remain discrete for long periods of time. Therefore, they exhibit significantly improved efficiency, even in the absence of a stabilizer such as oxybenzone, minimal to no migration across the skin, and good skin feel.

Kits

Further disclosed herein are kits that include the dispersions described herein. For example, provided herein is a kit that includes a first oil-in-water dispersion and a second oil-in-water dispersion. Each oil-in-water dispersion is composed of an oil phase that includes discrete oil particles coated with a solid material. The oil particles in the first dispersion can include an organic UVA absorber and are free of a UVB absorber. The oil particles in the second dispersion can include an organic UVB absorber and are free of a UVA absorber. In some cases, the oil particles in each of the first and second oil-in-water dispersions are present in an amount in a range from about 50 wt. % to about 80 wt. %, based on the total weight of each of the first and second oil-in-water dispersions. In various cases, each of the first and second oil-in-water dispersions are free of a metal oxide.

In some embodiments, the oil particles in the first and second dispersions consist essentially or, or consist of, a UVA absorber or a UVB absorber, as previously described herein.

In some embodiments, the kit includes a UVA absorber selected from the group consisting of avobenzone, oxybenzone, bemotrizinol, diethylamino hydroxybenzoyl methyl benzoate, and combinations thereof. For example, the UVA absorber can be avobenzone. In some cases, the UVA absorber is present in the discrete oil particle of the first oil-in-water dispersion in an amount in a range from about 10 wt. % to about 100 wt. %, based on the total weight of the oil particles in the first dispersion.

In various embodiments, the kit includes a UVB absorber selected from the group consisting of enzacamene, oxybenzone, octinoxate, octisalate, octyltriazone, homosalate, amiloxate, octocrylene, ensulizole, diethylhexyl butamido triazone, polysilicone 15, padimate 0, methylbenzylidene camphor, and combinations thereof. For example, the UVB absorber can be octinoxate. In some embodiments, the UVB absorber is present in the discrete oil particle of the second oil-in-water dispersion in an amount in a range from about 30 wt. % to about 100 wt. %, based on the total weight of the oil particles in the second dispersion.

In some cases, the oil particles in the first dispersion further comprise a photo stabilizer. The photo stabilizer can be selected from the group consisting of octocrylene, diethylhexyl naphthalate, undecylcrylene dimethicone, ethyl hexyl methoxycrylene, polyester-8, polyester 25, trimethoxybenzylidene pentanedione, diethylhexyl syringlidene malonate, tetramethyl hydroxy piperidinol, benzotriazole dodecyl p-cresol, sodium benzotriazole butyl phenol sulfonate, and combinations thereof. For example, the photo stabilizer can be octocrylene.

In some exemplary embodiments, the oil particles in the first dispersion are composed of avobenzone and octocrylene, and the oil particles in the second dispersion are composed of octinoxate.

Rinse-Off Compositions

The compositions described herein also are useful for rinse-off applications. As used herein, a "rinse-off" composition is one whereby the composition is ultimately rinsed or washed from a treated surface, such a skin or a hard surface, either during or after application of the composition to the surface. In some embodiments, the rinse-off compositions include the oil-in-water dispersions described herein, wherein the solid that coats the oil phase is a latex, such as nano latex or ethyl cellulose (e.g., AQUACOAT ECD by FMC Biopolymer).

Methods of Making the Sunscreen Compositions

The oil-in-water dispersions containing the UVA and UVB absorbers disclosed herein can be made by any method known in the art.

First, oil-in-water dispersions containing a liquid UVA absorber, and/or a liquid UVB absorber, and/or photostabilizer can be prepared as follows. The solid material is first dispersed in deionized water using a homogenizer at, e.g., 10K rpms for 5 minutes. If the solid material also includes a surface active polymer, the surface active polymer is added to the water and mixed until dissolved. The liquid UV absorber and optional photostabilizer are then slowly added to the resulting mixture and milled at, e.g., 10K rpms for 5 minutes, to result in the oil-in-water dispersion. Oil-in-water dispersions containing a crystalline UVA absorber and/or UVB absorber can be prepared similarly as those containing a liquid UVA and/or UVB absorber, except that the crystalline UV absorber is first added to a suitable solvent and heated (e.g., at 40° C.) until a clear solution results. The resulting solution is slowly added to the mixture containing the solid material and milled as described. Additional methods of preparing the dispersions disclosed herein can be found in the Examples section.

The oil-in-water dispersions that include the UVA and UVB absorbers can be added to an aqueous base (e.g., a hydrogel, an oil-in-water emulsion, or a water-in-oil emulsion) by any method known to one skilled in the art. For example, when the aqueous base is a hydrogel, a gelling agent is dispersed in water and mixed until uniform. Then, dispersions containing the UVB and/or UVA absorbers are each added to the mixture and mixed until uniform. When the sunscreen composition includes an SPF booster, a waterproofing agent, a photo stabilizer, or any of the other additives described herein, those materials are added to the sunscreen compositions by methods well known to those skilled in the art, and at commonly acceptable concentrations.

Thus, disclosed herein is a method of preparing a high efficiency sunscreen composition. In this method, an oil-in-water dispersion containing UVA and/or UVB absorbers described herein is combined with a base, such as a gel, a water-in-oil emulsion, or a water-in-oil emulsion. In embodiments wherein the UVA and UVB absorbers are enclosed within separate oil particles, a first oil-in-water dispersion containing an organic UVA absorber enclosed within a solid coating (i.e., a UVA absorber dispersion), and a second oil-in-water dispersion containing an organic UVB absorber enclosed within a solid coating (e.g., a UVB absorber dispersion) are each separately added and mixed (either sequentially in any order or simultaneously) into the same gelled aqueous base. The enclosed UVA absorber and the enclosed UVB absorber are maintained as separate oil particles after they are mixed in the same gelled aqueous base. In embodiments wherein the UVA and UVB absorbers are enclosed within the same oil particle, an oil-in-water dispersion containing both the organic UVA and UVB absorbers enclosed within a solid coating is mixed into a gelled aqueous base.

Additional methods of preparing the sunscreen compositions disclosed herein can be found in the Examples section.
Methods of Using the High Efficiency Sunscreen Compositions The high efficiency sunscreen compositions disclosed herein are able to both absorb and scatter UV radiation. Therefore, when the high efficiency sunscreen compositions disclosed herein coat a surface, they can reduce or limit the amount of UV radiation that contacts the surface. In embodiments wherein the UVA and UVB absorbers are maintained in separate solid-coated oil particles during manufacture and use of the high efficiency sunscreen composition, the absorbers do not interact, and thus destabilize each other. In embodiments wherein the UVA and UVB absorbers are enclosed within the same solid-coated oil particles, the oil particles can optionally include a photostabilizer to prevent the absorbers from interacting, and thus destabilizing, each other.

Accordingly, another aspect of the disclosure is a method of reducing contact of UV radiation on a surface. In this method the surface is coated with the high efficiency sunscreen composition disclosed herein, which includes an oil-in-water dispersion that includes an oil phase composed of discrete oil particles coated with a solid material and dispersed in an aqueous phase, wherein each oil particle contains a UVA and/or a UVB absorber, and optionally a photo stabilizer, and optionally, an aqueous base. The discrete oil particles remain intact after the sunscreen composition containing them contacts a surface, such as skin for at least about 4 hours, as previously described herein.

Yet another aspect of the disclosure is a method of photostabilizing interactive UVA and UVB absorbers by maintaining them separated in the process of manufacture. In this method, a first oil-in-water dispersion is formed by coating an oil particle containing a UVA absorber in a solid material. Before or after formation of the first oil-in-water dispersion, a second oil-in-water dispersion is formed by coating an oil particle containing a UVB absorber in a solid material. The first and second oil-in-water dispersions are then combined in the same aqueous phase sequentially (in any order) or simultaneously.

EXAMPLES

The following examples are provided for illustration and are not intended to limit the scope of the invention.

Example A: Preparation of UVA Absorber Dispersions

Oil-in-water dispersions containing an organic UVA absorber (and no UVB absorber) in the oil phase were prepared as follows. The UVA absorber was dissolved in the solvent and mixed at 40° C. until the solution became clear. The solid coating material was then dispersed in deionized water using a homogenizer at 10K rpms for 5 minutes. If a surface active polymer was used, it was added to the solid coating mixture and mixed until soluble. The UVA absorber solution was then added to the solid coating mixture, and the resulting mixture was milled at 10K rpms for 5 minutes, or until uniform. If an excipient was present, such as a water proofing polymer, a preservative, a humectant, a thickeners, a chelating agent, and/or a surfactant having a low HLB, then it was added to the mixture and mixed until uniform.

When OLEOCRAFT HP-31 was used as the solid coating material, it was dispersed in deionized water and mixed at 90° C. until the solution became clear. The UVA absorber solution was then added to the solid coating mixture while rapidly cooling to 30° C. If a waterproofing polymer and/or preservative were present, then they were added as previously described.

Various UVA absorber dispersions that were formed can be found in Table 1, below.

Example B: Preparation of UVB Absorber Dispersions

Oil-in-water dispersions containing an organic UVB absorber (and no UVA absorber) in the oil phase were prepared as follows. The solid coating material was dispersed in deionized water using a homogenizer at 10K rpms for 5 minutes. If a surface active polymer or cationic composite was used, it was added to the solid coating mixture and mixed until soluble. The UVB absorber was then slowly added to the mixture, and the resulting mixture was milled at 10K rpms for 5 minutes. If an excipient was present, such as a water proofing polymer, a preservative, a humectant, a thickeners, a chelating agent, and/or a surfactant having a low HLB, then it was added to the mixture and mixed until uniform. If octyl triazone was used as the UVB absorber, then it was heated in the solvent at 40° C. until clear, before being added to the solid coating mixture.

Various UVB absorber dispersions that were formed can be found in Table 2, below.

Example C: Preparation of UVA/UVB Absorber Dispersions

Oil-in-water dispersions containing both an organic UVA absorber and a UVB absorber in the same oil particle were prepared as follows. The solid coating material was dispersed in deionized water using a homogenizer at 10K rpms for 5 minutes. If a surface active polymer or cationic composite was used, it was added to the solid coating mixture and mixed until soluble. The UV absorbers and optional photostabilizer were then slowly added to the mixture, and the resulting mixture was milled at 10K rpms for 5 minutes. If an excipient was present, such as a water proofing polymer, a preservative, a thickeners, a chelating agent, and/or a surfactant having a low HLB, then it was added to the mixture and mixed until uniform. If octyl triazone was used as the UVB absorber, then it was heated in the solvent at 40° C. until clear, before being added to the solid coating mixture.

Various UVA/UVB absorber dispersions that were formed can be found in Table 3, below.

Example D: Preparation of Photostabilizer Dispersions

Oil-in-water dispersions containing an organic UVA photostabilizer in the oil phase were prepared as follows. The solid coating material was dispersed in deionized water using a homogenizer at 10K rpms for 5 minutes. If a surface active polymer was used, it was added to the solid coating mixture and mixed until soluble. The photostabilizer was heated at 40° C. until clear. The photostabilizer was then slowly added to the solid coating material mixture, and the resulting mixture was milled at 10K rpms for 5 minutes. If a preservative was present, then it was added to the mixture and mixed until uniform.

For example, a photostabilizer dispersion included 1.5 wt. % LAPONITE XLG (solid coating material), 1.0% GANEX P904 LC (surface active polymer), 46.5% deionized water, 50.0 wt. % SOLASTAY S1 (photostabilizer), and 1.0% EUXYL K900 (preservative).

Example E: Preparation of High Efficiency Sunscreen Compositions

High efficiency sunscreen compositions were prepared as follows. A gelling agent (for a hydrogel base) or an oil (for an oil-in-water emulsion) was dispersed into deionized water, and the emulsion was mixed until uniform. For a water-in-oil emulsion, deionized water was dispersed into an oil and the emulsion was mixed until uniform. The UVA, UVB, and UVA/UVB dispersions were then added and mixed until uniform. If sodium hydroxide was present, then it was added to the mixture and mixed until uniform. If an excipient, such as preservative was present, then it was added to the mixture and mixed until uniform.

Various high efficiency sunscreen compositions that were formed can be found in Table 4, below.

Example F: Stability Testing of the Dispersions

Stability testing was performed by putting 4 oz samples of the dispersions in glass at 45° C. for 3 months and in 3 freeze/thaw cycles (−20° C. to room temperature). Samples were observed for changes in physical appearance, chemical stability, and SPF changes. The success criteria at 45° C. for 3 months was 95%+ chemical stability, +−10% change in in vivo SPF, and no significant change in appearance. The freeze/thaw success criteria was no significant change in appearance and no active crystallization after 3 freeze thaw cycles.

Example F: Stability Testing of the Dispersions

Stability testing was performed by putting 4 oz samples of the dispersions in glass at 45° C. for 3 months and in 3 freeze/thaw cycles (−20° C. to room temperature). Samples were observed for changes in physical appearance, chemical stability, and SPF changes. The success criteria at 45° C. for 3 months was 95%+ chemical stability, +−10% change in in vivo SPF, and no significant change in appearance. The freeze/thaw success criteria was no significant change in appearance and no active crystallization after 3 freeze thaw cycles.

TABLE 1

UVA Absorber Dispersions

| | A1 | A2 | A3 | A4 | A5 | A6 | A7 | A8 | A9 | A10 | A11 | A12 | A14 | A15 |
|---|---|---|---|---|---|---|---|---|---|---|---|---|---|---|
| | | | | | | wt. % | | | | | | | | |
| UVA Absorber | | | | | | | | | | | | | | |
| Avobenzone | 5.0 | 7.0 | 7.0 | 20.0 | 20.0 | | 20.0 | | 7.0 | 7.5 | | 25.0 | 15.0 | 20.0 |
| Diethylamino Hydroxybenzoyl Hexyl Benzoate | | | | | | 20.0 | | 20.0 | | | | | | |
| Oxybenzone | | | | | | | | | | | | 20.0 | | |
| Solvent | | | | | | | | | | | | | | |
| $C_{12-15}$ alcohol benzoate | 45.0 | 43.0 | 43.0 | | | | | | 43.0 | | | | | |
| PELEMOL BIP | | | | 30.0 | 30.0 | | 30.0 | | | 10.0 | 30.0 | 35.0 | | 40.0 |
| Isodecyl salicylate | | | | | 30.0 | | 30.0 | | | | | | | |
| FINSOLV PG22 | | | | | | | | | | | | | 45.0 | |

TABLE 1-continued

UVA Absorber Dispersions

| | A1 | A2 | A3 | A4 | A5 | A6 | A7 | A8 | A9 | A10 | A11 | A12 | A14 | A15 |
|---|---|---|---|---|---|---|---|---|---|---|---|---|---|---|
| | | | | | | wt. % | | | | | | | | |
| *Solid Coating Material* | | | | | | | | | | | | | | |
| SOBIND HARMONY SOPRANO | 7.5 | | 1.0 | | | | 5.0 | | | | | | | |
| LAPONITE XLG | | 1.0 | | 1.0 | | | | | | | 1.5 | | | |
| AQUACOAT ECD | | | 25.0 | | 20.0 | 25.0 | | | | | | | 10.0 | 10.0 |
| EXCELLION EM6 | | | | | | | 2.0 | | | | | | | |
| AEROSIL 300 | | | | | | | | | 2.0 | | | | | |
| OLEOCRAFT HP-31 | | | | | | | | | | 12.5 | | | | |
| *Surface Active Polymer* | | | | | | | | | | | | | | |
| GANEX P904 LC | | 0.9 | | | | | | | 0.9 | | 1.0 | 5.0 | | |
| *Preservative* | | | | | | | | | | | | | | |
| EUXYL K900 | | 1.0 | 1.0 | 1.0 | | 1.0 | | 1.0 | 1.0 | 1.0 | 1.0 | | | |
| EUXYL PE9010 | | | | | | | 1.0 | | | | | 0.2 | | |
| LEXGUARD O | | | | | | | | | | | | | 0.5 | 0.5 |
| *Humectant* | | | | | | | | | | | | | | |
| Glycerin | | | | | | | | | | | | | 15.0 | 15.0 |
| *Chelating Agent* | | | | | | | | | | | | | | |
| Disodium EDTA | | | | | | | | | | | | | | 0.1 |
| *Thickener* | | | | | | | | | | | | | | |
| ARISTOFLEX AVC | | | | | | | | | | | | | 0.1 | 0.1 |
| Deionized water | 42.5 | 47.1 | 24.0 | 47.0 | 30.0 | 24.0 | 47.0 | 44.0 | 46.1 | 69.0 | 46.5 | 34.8 | 14.4 | 14.3 |

TABLE 2

UVB Absorber Dispersions

| | B1 | B2 | B3 | B4 | B5 | B6 | B7 | B8 | B9 | B10 | B11 | B12 |
|---|---|---|---|---|---|---|---|---|---|---|---|---|
| | | | | | | wt. % | | | | | | |
| *UVB Absorber* | | | | | | | | | | | | |
| Octinoxate | 50.0 | 50.0 | 50.0 | 50.0 | 50.0 | | | 50.0 | 50.0 | 80.0 | 60.0 | 40.0 |
| Octyl Triazone | | | | | | 10.0 | 10.0 | | | | | |
| Octocrylene | | | | | | | | | | | | 20.0 |
| *Solid Coating* | | | | | | | | | | | | |
| SOBIND HARMONY SOPRANO | 7.5 | | | 1.0 | | | | | | | | |
| LAPONITE XLG | | 1.0 | | 1.0 | | 1.0 | 1.0 | | | | 10.0 | 10.0 |
| AQUACOAT ECD | | | 25.0 | | | | | | | | 10.0 | 10.0 |
| EXCELLION EM6 | | | | | 2.0 | | | | | | | |
| AEROSIL 300 | | | | | | | | 2.0 | 2.0 | | | |
| *Surface Active Polymer* | | | | | | | | | | | | |
| GANEX P904 LC | | 0.9 | | | | 1.0 | 1.0 | 0.9 | | 5.0 | | |
| Lauryl Laurate | | | | | | 40.0 | 40.0 | | | | | |
| *Cationic Composite* | | | | | | | | | | | | |
| Cetyl trimonium chloride | | | | | | | | | 0.2 | | | |
| *Preservative* | | | | | | | | | | | | |
| Euxyl K900 | | 1.0 | 1.0 | 1.0 | 1.0 | | | | | | | |
| EUXYL PE9010 | | | | | | 1.0 | 1.0 | 1.0 | 1.0 | 0.2 | | |
| LEXGUARD O | | | | | | | | | | | 0.5 | 0.5 |
| *Humectant* | | | | | | | | | | | | |
| Glycerin | | | | | | | | | | | 15.0 | 15.0 |
| *Thickener* | | | | | | | | | | | | |
| ARISTOFLEX AVC | | | | | | | | | | | 0.1 | 0.1 |
| Deionized water | 42.5 | 47.1 | 24.0 | 47.0 | 47.0 | 45.9 | 47.0 | 46.1 | 46.8 | 14.8 | 14.4 | 14.4 |

TABLE 3

UVA and UVB Absorber Dispersions

|  | C1 wt. % | C2 | C3 |
|---|---|---|---|
| UVA Absorber | | | |
| Avobenzone | 15.0 | 15.0 | 15.0 |
| UVB Absorber | | | |
| Octinoxate | | | 30.0 |
| Octocrylene | 35.0 | 30.0 | 15.0 |
| Solvent | | | |
| FINSOLV EB | | 5.0 | |
| Low HLB Emulsifier | | | |
| Hexglyn PR15 | | 10.0 | 10.0 |
| Solid Coating Material | | | |
| AQUACOAT ECD | 20.0 | 10.0 | 10.0 |
| Preservative | | | |
| EUXYL K900 | 1.0 | | |
| Humectant | | | |
| LEXGUARD O | | 0.5 | 0.5 |
| Glycerin | | 15.0 | 15.0 |
| Chelating Agent | | | |
| Disodium EDTA | | 0.1 | 0.1 |
| Thickener | | | |
| ARISTOFLEX AVC | | 0.1 | 0.1 |
| Deionized water | 19.0 | 14.3 | 14.3 |

TABLE 4

High Efficiency Sunscreen Compositions

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
|  | | | | | | | wt. % | | | | | | | |
| Dispersion A | | | | | | | | | | | | | | |
| A1 | 12.5 | | | | | | | | | | | | | |
| A2 | | 7.1 | | | | | | | | | | | | |
| A3 | | | 7.1 | | | | 15.0 | | | | | | | |
| A4 | | | | 2.5 | | | | | | | | | | |
| A9 | | | | | 7.0 | | | | | | | | | |
| A10 | | | | | | 7.1 | | | | | | | | |
| A12 | | | | | | | | 2.0 | | | | | | |
| A14 | | | | | | | | | | | | | 13.3 | |
| Dispersion B | | | | | | | | | | | | | | |
| B1 | 4.0 | | | | | | | | | | | | | |
| B2 | | 4.0 | | | | | | | | | | | | |
| B3 | | | 4.0 | | | | | | | | | | | |
| B4 | | | | 4.0 | | 4.0 | | | | | | | | |
| B8 | | | | | 4.0 | | | | | | | | | |
| B10 | | | | | | | | 2.5 | | | | | | |
| B11 | | | | | | | | | | | | | | 3.4 |
| B12 | | | | | | | | | | | | 5.0 | | |
| Dispersion C | | | | | | | | | | | | | | |
| C1 | | | | | | | | | 10.0 | | | 10.0 | | |
| C2 | | | | | | | | | | 10.0 | | | | 10.0 |
| Gelling Agent | | | | | | | | | | | | | | |
| ARISTOFLEX AVC | 1.1 | 1.15 | 1.15 | | 1.15 | 1.15 | 1.15 | 1.15 | 1.15 | 1.15 | 1.15 | 1.15 | 1.15 | 1.15 |
| ULTREZ 21 | | | | 0.27 | | | | | | | | | | |
| Preservative | | | | | | | | | | | | | | |
| GEOGARD | 0.4 | | | | | | | | | | | | | |
| EUXYL PE 9010 | | 0.9 | | 0.9 | | 0.9 | 0.9 | 1.0 | 1.0 | 1.0 | 1.0 | 1.0 | 1.0 | 1.0 |
| EUXYL K900 | | | | | 1.0 | | | | | | | | | |
| Sodium Hydroxide | | | | 0.30 | | | | | | | | | | |
| Deionized Water | 82.0 | 86.85 | 86.85 | 92.03 | 86.85 | 86.85 | 82.95 | 93.35 | 91.15 | | 77.85 | 79.55 | 87.85 | 84.55 |
| Results | | | | | | | | | | | | | | |
| UVA Absorber-Final Concentration | 0.5 | 0.5 | 0.5 | 0.5 | 0.5 | 0.5 | 3.0 | 0.5 | 1.5 | 1.5 | 2.0 | 1.5 | 1.5 | |
| UVB Absorber-Final Concentration | 2.0 | 2.0 | 2.0 | 2.0 | 2.0 | 2.0 | | 2.0 | 3.5 | 3.0 | 3.0 | 4.5 | 5.0 | |

TABLE 4-continued

High Efficiency Sunscreen Compositions

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| | | | | | | | | wt. % | | | | | | |
| in vivo SPF* | 32.3 | 30 | 32.3 | 32.3 | 18 | 26.2 | 33 | >20** | >40** | | 32 | >43** | >51** | 53 |
| in vivo SPF Efficiency (SPF units per 1% sunscreen) | 12.9 | 12 | | | 7.2 | 10.5 | 11.0 | 8 | 8 | | 7.1 | | | 8.2 |

*methods of determining SPF values are globally standard and can be found in, for example, the Federal Register, Department of Health and Human Services, Food and Drug Administration, Vol. 76, No. 117, Jun. 17, 2011.
**estimated using an in vivo SPF efficiency of 8 units per 1% sunscreen by methods known to those skilled in the art Exemplary Embodiments Exemplary embodiment G provides a sunscreen composition comprising an organic UVA absorber and an organic UVB absorber, the UVA absorber and the UVB absorber each separately enclosed within discrete oil particles coated with a solid material and dispersed within an aqueous phase; wherein:

the enclosed UVA and UVB absorbers each (a) absorb UV irradiation, and (b) scatter UV irradiation;
the enclosed UVA absorber is present in a concentration in a range from about 10 wt. % to about 100 wt. %, based on the total weight of the oil particle;
the enclosed UVB absorber is present in a concentration in a range from about 20 wt. % to 100 wt %, based on the total weight of the oil particle; and
the composition exhibits an in vivo SPF efficiency of at least about 8 SPF units per 1 wt. % sunscreen. Below provides exemplary variations to embodiment G.

The composition of the preceding paragraph, wherein the oil particles have a particle size in a range from about 0.5 μm to about 200 μm.

The composition of the preceding paragraph, wherein the oil particles have a particle size in a range from about 0.5 μm to about 100 μm.

The composition of the preceding paragraph, wherein the oil particles have a particle size in a range from about 0.5 μm to about 10 μm.

The composition of any one of the above variations of embodiment G, wherein the enclosed UVA absorber is present in a concentration in a range from about 30 wt. % to about 100 wt. %, based on the total weight of the oil particle.

The composition of the preceding paragraph, wherein the enclosed UVA absorber is present in a concentration in a range from about 50 wt. % to about 100 wt. %, based on the total weight of the oil particle.

The composition of any one of the above variations of embodiment G, wherein the enclosed UVB absorber is present in a concentration in a range from about 40 wt. % to about 100 wt %, based on the total weight of the oil particle.

The composition of the preceding paragraph, wherein the enclosed UVB absorber is present in a concentration in a range from about 60 wt. % to about 100 wt %, based on the total weight of the oil particle.

The composition of any one of the above variations of embodiment G, wherein the in vivo SPF efficiency is at least about 10 SPF units per 1 wt. % sunscreen.

The composition of the preceding paragraph, wherein the in vivo SPF efficiency is at least about 15 SPF units per 1 wt. % sunscreen.

The composition of the preceding paragraph, wherein the in vivo SPF efficiency is at least about 20 SPF units per 1 wt. % sunscreen.

The composition of any one of the above variations of embodiment G, wherein the oil particles are present in a concentration in a range from about 30 wt. % to about 70 wt. %, based on the total weight of the oil particles and aqueous phase.

The composition of the preceding paragraph, wherein the oil particles are present in a concentration in a range from about 50 wt. % to about 60 wt. %, based on the total weight of the oil particles and aqueous phase.

The composition of any one of the above variations of embodiment G, wherein the oil particles remain discrete when the composition contacts skin for at least about 4 hours.

The composition of the preceding paragraph, wherein the oil particles remain discrete when the composition contacts the skin for at least about 8 hours.

The composition of any one of the above variations of embodiment G, wherein the solid material is selected from the group consisting of nano latex, colloidal silica, fumed silica, zeolite, natural clay, synthetic clay, ethyl cellulose, microcrystalline cellulose, cyclodextrin, vegetable protein, sodium caseinate, inulin lauryl carbamate, sodium octenylsuccinate starch, sodium octenylsuccinate phytoglycogen, and combinations thereof.

The composition of the preceding paragraph, wherein the solid material is selected from the group consisting of sodium magnesium silicate, colloidal silica, fumed silica, lithium magnesium sodium silicate and combinations thereof.

The composition of the preceding paragraph, wherein the solid material is part of a complex comprising a cationic material selected from the group consisting of cetyl trimonium chloride, polyquaternium-59, methoxy cinnamidopropyl laurdimonium, methoxycinnamidopropyl hydroxy sultaine, dimethylpabamidopropyl laurdimonium tosylate, and combinations thereof.

The composition of any one of the above variations of embodiment G, wherein the solid material further comprises an emulsion stabilizing, water-soluble, surface active polymer.

The composition of the preceding paragraph, wherein the surface active polymer has a molecular weight greater than about 1000 Daltons and a surface tension in a range from about 15 nM/m to about 60 nM/m at 0.1 wt. % at 25° C.

The composition of either of the preceding two paragraphs paragraph, wherein the surface active polymer is selected from the group consisting of mono alkyl esters of poly(methyl vinyl ether/maleic acid) sodium salt and alkylated polyvinylpyrrolidone; terephthalate polyesters; and combinations thereof.

The composition of the preceding paragraph, wherein the surface active polymer is selected form the group consisting of butylated polyvinylpyrrolidone; monobutyl ethylester of poly(methyl vinyl ether/maleic acid) copolymer, sodium salt; and combinations thereof.

The composition of any one of the above variations of embodiment G, wherein the UVA absorber is selected from the group consisting of bemotrizinol, avobenzone, bisdisulizole disodium, meradimate, bisoctotrizole, ecamisule, diethylamino hydroxybenzoyl methyl benzoate, drometrizole trisiloxane and combinations thereof.

The composition of the preceding paragraph, wherein the UVA absorber is selected from the group consisting of avobenzone, oxybenzone, bemotrizinol, diethylamino hydroxybenzoyl methyl benzoate, and combinations thereof.

The composition of any one of the above variations of embodiment G, wherein the UVB absorber is selected from the group consisting of enzacamene, oxybenzone, octinoxate, octisalate, octyltriazone, homosalate, amiloxate, octocrylene, ensulizole, diethylhexyl butamido triazone, polysilicone 15, padimate O, and combinations thereof.

The composition of the preceding paragraph, wherein the UVB absorber is selected from the group consisting of octinoxate, octocrylene, diethylhexyl butamido triazone, octyltriazone, and combinations thereof.

The composition of any one of the above variations of embodiment G, wherein the aqueous phase comprises a gelling agent.

The composition of the preceding paragraph, wherein the gelling agent is selected from the group consisting of crosslinked acrylate, crosslinked acrylic acid, crosslinked polyvinylpyrrolidone (PVP), polyamide-3, and combinations thereof.

The composition of the preceding paragraph, wherein the gelling agent is selected from the group consisting of acrylates/$C_{10-30}$ alkyl acrylate crosspolymer, ammonium or sodium acryloyldimethyltaurate/vp copolymer, hydroxyethylacrylate/sodium acryloyldimethyltaurate copolymer, crosslinked polyvinylpyrrolidone, and combinations thereof.

The composition of the preceding paragraph, wherein the gelling agent is sodium or ammonium acryloyldimethyltaurate/vinylpyrrolidone (VP) copolymer.

The composition of any one of the above variations of embodiment G, wherein the composition is free of a photostabilizer.

The composition of any one of the above variations of embodiment G (excluding the above paragraph), wherein the composition further comprises a photostabilizer.

The composition of the preceding paragraph, wherein the photostabilizer is selected from the group consisting of diethylhexyl naphthalate, undecylcrylene dimethicone, ethyl hexyl methoxycrylene, polyester-8, polyester 25, trimethoxybenzylidene pentanedione, diethylhexyl syringlidene malonate, tetramethyl hydroxy piperidinol, benzotriazole dodecyl p-cresol, sodium benzotriazole butyl phenol sulfonate, and combinations thereof.

The composition of any one of the above variations of embodiment G, wherein the composition is free from a microfine metal oxide.

The composition of any one of the above variations of embodiment G further comprising an additive selected from the group consisting of a preservative, a SPF booster, a waterproofing polymer, an emollient, a powder, a fragrance, a chelating agent, and combinations thereof.

A method of reducing contact of UV radiation on a surface comprising coating said surface with the sunscreen composition of embodiment G.

A method of photostabilizing interactive UVA and UVB absorbers by maintaining them separated as discrete particles in the process of manufacture, the method comprising:
  forming a first oil-in-water dispersion containing an organic UVA absorber encapsulated within a solid coating in an aqueous phase;
  forming a second oil-in-water dispersion containing an organic UVB absorber encapsulated within a solid coating in an aqueous phase;
  combining the first oil-in-water dispersion and the second oil-in-water dispersion in a gelled aqueous phase; and
  maintaining the encapsulated UVA absorber and the encapsulated UVB absorber separated as discrete particles.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. An oil-in-water dispersion comprising:
  an oil phase comprising discrete oil particles, each oil particle coated with a solid material, and each oil particle comprising:
    (i) an organic UVA absorber, and
    (ii) an organic UVB absorber,
  wherein:
  the oil-in-water dispersion is free of a metal oxide;
    the UVA absorber is present in an amount in a range from about 10 wt. % to about 70 wt. %, based on the total weight of the oil particle;
    the UVB absorber is present in an amount in a range from about 30 wt. % to about 90 wt. %, based on the total weight of the oil particle; and the oil particles are present in an amount in a range from about 50 wt. % to about 80 wt. %, based on the total weight of the dispersion.

2. The dispersion of claim 1, wherein the UVB absorber is octocrylene, octinoxate, homosalate, octisalate, or octyltriazone, or combinations thereof.

3. The dispersion of claim 1, wherein each discrete particle further comprises a photostabilizer in an amount in a range of about 10 wt. % to about 20 wt. %, based on the total weight of the oil particle.

4. The dispersion of claim 3, wherein the photostabilizer is octocrylene, diethylhexyl naphthalate, undecylcrylene dimethicone, ethyl hexyl methoxycrylene, polyester-8, polyester 25, trimethoxybenzylidene pentanedione, diethylhexyl syringlidene malonate, tetramethyl hydroxy piperidinol, benzotriazole dodecyl p-cresol, or sodium benzotriazole butyl phenol sulfonate, or combinations thereof.

5. The dispersion of claim 1, wherein the UVA absorber is avobenzone and the UVB absorber is octocrylene.

6. An oil-in-water dispersion comprising:
an oil phase comprising first discrete oil particles, second discrete oil particles, or both first and second discrete oil particles, each oil particle coated with a solid material, the first oil particles comprising an organic UVA absorber and being free of a UVB absorber, the second oil particles comprising an organic UVB absorber and being free of a UVA absorber;
wherein:
the oil-in-water dispersion is free of a metal;
the UVA absorber is present in an amount in a range from about 10 wt. % to about 100 wt. %, based on the total weight of the first oil particles;
the UVB absorber is present in an amount in a range from about 30 wt. % to about 100 wt. %, based on the total weight of the second oil particles; and
the oil particles are present in an amount in a range from about 50 wt. % to about 80 wt. %, based on the total weight of the dispersion;
wherein the solid material comprises an emulsion stabilizing, water-soluble, surface active polymer.

7. The dispersion of claim 6, wherein the oil particles have a particle size in a range from about 0.5 μm to about 200 μm.

8. The dispersion of claim 6, wherein the first discrete oil particles further comprise a photostabilizer in an amount in a range of about 10 wt. % to about 20 wt. % based on the total weight of the oil particle.

9. The dispersion of claim 8, wherein the photostabilizer is octocrylene, diethylhexyl naphthalate, undecylcrylene dimethicone, ethyl hexyl methoxycrylene, polyester-8, polyester 25, trimethoxybenzylidene pentanedione, diethylhexyl syringlidene malonate, tetramethyl hydroxy piperidinol, benzotriazole dodecyl p-cresol, or sodium benzotriazole butyl phenol sulfonate, or combinations thereof.

10. The dispersion of claim 6, wherein the UVA absorber is bemotrizinol, avobenzone, bisdisulizole disodium, meradimate, bisoctotrizole, ecamisule, diethylamino hydroxybenzoyl methyl benzonate, drometrizole trisiloxane and combinations thereof; and the UVB absorber is selected from the group consisting of enzacamene, oxybenzone, octinoxate, octisalate, octyltriazone, homosalate, amiloxate, octocrylene, ensulizole, diethylhexyl butamido triazone, polysilicone 15, padimate O, or methylbenzylidene camphor, or combinations thereof.

11. The dispersion of claim 6, wherein the dispersion comprises second discrete oil particles, and the UVB absorber is octinoxate.

12. The dispersion of claim 6, wherein the dispersion further comprises one or more of a humectant, a thickener, a chelating agent, and a surfactant having an HLB value in a range of about 2 to about 6.

13. The dispersion of claim 6, wherein the dispersion exhibits an in vivo SPF efficiency of at least about 6 SPF units per 1 wt. % sunscreen.

14. The dispersion of claim 6, wherein the discrete oil particles remain discrete for at least about 4 hours after contact with a surface.

15. The dispersion of claim 6, wherein the dispersion is stable at −15° C. for three freeze-thaw cycles and at 45° C. for one month, characterized by:
(i) maintaining at least 95% of its chemical activity, or
(ii) maintaining at least 95% of its SPF value, or
(iii) exhibiting no crystallization, or
(iv) exhibiting no change in physical appearance.

16. A sunscreen composition comprising the dispersion of claim 6 and an aqueous sunscreen base.

17. The composition of claim 16 wherein the aqueous sunscreen base is a hydrogel, an oil-in-water emulsion, or a water-in-oil emulsion.

18. The composition of claim 16, wherein the aqueous base is free of a metal oxide.

19. The composition of claim 16, further comprising an additive selected from the group consisting of a preservative, a SPF booster, a waterproofing polymer, an emollient, a powder, a fragrance, a chelating agent, and combinations thereof.

20. A kit comprising a first oil-in-water dispersion, a second oil-in-water dispersion, or both a first and second oil-in-water dispersion; each oil-in-water dispersion comprising an oil phase comprising discrete oil particles, each oil particle coated with a solid material;
the oil particles in the first dispersion comprising an organic UVA absorber and being free of a UVB absorber;
the oil particles in the second dispersion comprising an organic UVB absorber and being free of a UVA absorber;
wherein:
each oil-in-water dispersion is free of a metal;
the UVA absorber is present in an amount in a range from about 10 wt. % to about 100 wt. %, based on the total weight of the oil particles in the first dispersion;
the UVB absorber is present in an amount in a range from about 30 wt. % to about 100 wt. %, based on the total weight of the oil particles in the second dispersion; and
the oil particles in each of the first and second oil-in-water dispersions are present in an amount in a range from about 50 wt. % to about 80 wt. %, based on the total weight of each of the first and second oil-in-water dispersion;
wherein the solid material comprises an emulsion stabilizing, water-soluble, surface active polymer.

21. A method of reducing contact of UV radiation on a surface comprising coating said surface with the dispersion of claim 6.

22. A method of photostabilizing interactive UVA and UVB absorbers by maintaining them separated as discrete particles in the process of manufacture, the method comprising:
forming a first oil-in-water dispersion containing an oil particle comprising an organic UVA absorber coated with a solid material;
forming a second oil-in-water dispersion containing an oil particle comprising an organic UVB absorber coated with a solid material; combining the first oil-in-water dispersion and the second oil-in-water dispersion in an aqueous base; and maintaining the oil particles from the first and second oil-in-water dispersions as discrete particles, wherein the solid material comprises an emulsion stabilizing, water-soluble, surface active polymer.

23. The dispersion of claim 6, wherein the surface active polymer has a molecular weight greater than 1000 D.

24. The dispersion of claim 6, wherein the coated oil particles stack on top of each other when applied to a surface, wherein said stacking increases a film thickness and increases an optical path length that UV needs to travel to reach the surface.

25. The dispersion of claim 6, wherein the concentration of UVA absorber is 0.5 to 2 wt. % of the total weight composition; the concentration of the UVB absorber is 2.0-4.5 wt. % of the total weight composition, and the in vivo SPF efficiency is from 7-13 SPF units per 1% sunscreen.

26. The dispersion of claim 6, wherein the solid material is acrylate nano latex, fumed silica, cetyl silica silylate, zeolite, natural clay, synthetic clay, ethyl cellulose, microcrystalline cellulose, cyclodextrin, vegetable protein, sodium caseinate, inulin lauryl carbamate, sodium octenylsuccinate starch, or sodium octenylsuccinate phytoglycogen, or combinations thereof.

* * * * *